US008696760B2

(12) United States Patent
Bertram et al.

(10) Patent No.: US 8,696,760 B2
(45) Date of Patent: *Apr. 15, 2014

(54) SCAFFOLDS FOR ORGAN RECONSTRUCTION AND AUGMENTATION

(75) Inventors: Timothy A. Bertram, Winston-Salem, NC (US); Andrew Bruce, Lexington, NC (US); Deepak Jain, Winston-Salem, NC (US); Manuel J. Jayo, Winston-Salem, NC (US); John W. Ludlow, Carrboro, NC (US); Darell McCoy, Clemmons, NC (US); Richard Payne, Winston-Salem, NC (US); Namrata D. Sangha, Winston-Salem, NC (US); Oluwatoyin A. Knight, Winston-Salem, NC (US)

(73) Assignee: Tengion, Inc., Winston-Salem, NC (US)

( * ) Notice: Subject to any disclaimer, the term of this patent is extended or adjusted under 35 U.S.C. 154(b) by 166 days.

This patent is subject to a terminal disclaimer.

(21) Appl. No.: 13/037,559

(22) Filed: Mar. 1, 2011

(65) Prior Publication Data

US 2011/0257726 A1      Oct. 20, 2011

Related U.S. Application Data

(63) Continuation of application No. 11/706,081, filed on Feb. 12, 2007, now Pat. No. 7,918,897.

(60) Provisional application No. 60/772,754, filed on Feb. 10, 2006.

(51) Int. Cl.
*A61F 2/04* (2013.01)

(52) U.S. Cl.
USPC .................. 623/23.65; 623/23.64; 623/23.66; 623/23.71; 424/422; 424/484; 424/486; 424/487; 424/93.7; 435/373

(58) Field of Classification Search
None
See application file for complete search history.

(56) References Cited

U.S. PATENT DOCUMENTS

| 3,953,897 A | 5/1976 | Chevallet et al. |
| 5,514,378 A | 5/1996 | Mikos et al. |

(Continued)

FOREIGN PATENT DOCUMENTS

| WO | WO 96/31232 | 10/1996 |
| WO | WO 97/37614 | 10/1997 |

(Continued)

OTHER PUBLICATIONS

Ashkar, L. and Heller, E., J. Urol., vol. 98, pp. 679-683 (1967).
Atala, A. et al., J. Urol., vol. 148 (2 Pt 2), pp. 658-662 (1992).
Atala, A., et al. J. Urol., vol. 150 (2 Pt 2), pp. 608-612 (1993).

(Continued)

*Primary Examiner* — Allison Ford
(74) *Attorney, Agent, or Firm* — Jeffery P. Bernhardt; Arnold & Porter LLP

(57) ABSTRACT

Biocompatible synthetic or natural scaffolds are provided for the reconstruction, repair, augmentation or replacement of organs or tissue structures in a patient in need of such treatment. The scaffolds are shaped to conform to at least a part of the organ or tissue structure and may be seeded with one or more cell populations. Inserts, receptacles and ports are also provided for the attachment of tubular vessels to the neo-organ scaffolds. The seeded scaffolds are implanted into the patient at the site in need of treatment to form an organized organ or tissue structure. The scaffolds may be used to form organs or tissues, such as bladders, urethras, valves, and blood vessels.

38 Claims, 32 Drawing Sheets
(19 of 32 Drawing Sheet(s) Filed in Color)

(56) References Cited

U.S. PATENT DOCUMENTS

| | | | |
|---|---|---|---|
| 5,586,438 | A | 12/1996 | Fahy |
| 5,645,806 | A | 7/1997 | Hess et al. |
| 5,654,273 | A | 8/1997 | Gallo et al. |
| 5,762,966 | A | 6/1998 | Knapp, Jr. et al. |
| 6,296,019 | B1 | 10/2001 | Muller et al. |
| 6,296,668 | B1 | 10/2001 | Desgrandchamps et al. |
| 6,416,995 | B1 | 7/2002 | Wolfinbarger |
| 6,428,802 | B1 | 8/2002 | Atala |
| 6,576,019 | B1 | 6/2003 | Atala et al. |
| 7,131,996 | B2 | 11/2006 | Wasserman et al. |
| 7,479,161 | B1 | 1/2009 | Wasserman et al. |
| 7,806,937 | B2 * | 10/2010 | Atala et al. ................. 623/23.64 |
| 2002/0193884 | A1 | 12/2002 | Wasserman et al. |
| 2004/0029266 | A1 | 2/2004 | Barbera-Guillem |
| 2005/0002982 | A1 | 1/2005 | Mooney et al. |
| 2007/0073413 | A1 | 3/2007 | Wasserman et al. |

FOREIGN PATENT DOCUMENTS

| | | | |
|---|---|---|---|
| WO | WO 98/35633 | | 8/1998 |
| WO | WO 99/22781 | | 10/1998 |
| WO | WO 99/01538 | * | 1/1999 |
| WO | WO 00/56246 | | 9/2000 |
| WO | WO 01/49827 | | 7/2001 |

OTHER PUBLICATIONS

Atala, A., J. Urol., vol. 156 (2 Pt 1), pp. 338-339 (1996).
Craig P. H., Williams J. A., Davis K. W., et al.: A Biological Comparison of Polyglactin 910 and Polyglycolic Acid Synthetic Absorbable Sutures. Surg., vol. 141, No. 1, pp. 1-7, (1975).
Fauza et al., J. Ped. Surg., vol. 33, pp. 7-12 (1998).
Ishaug et al., J Biomed Mater Res.; 36(1):17-28 (1997).
Kelami, A. et al., J. Urol., vol. 104 No. 5, pp. 693-698 (1970).
Kelami, A. et al., J. Urol., vol. 105, No. 4, pp. 518-522 (1971).
Kirker-Head, C. A. Vet. Surg., vol. 24, pp. 408-419 (1995).
Kudish, H. G., J. Urol., vol. 78, No. 3, pp. 232-235 (1957).
Laurencin, C. T. et al., J Biomed Mater. Res., vol. 30, pp. 133-138 1996.
Zdrahala, R. J., J. Biomater. Appl., vol. 10, pp. 309-329 (1996).
Falke, G., et al., "Tissue Engineering of the Bladder", World J. Urol., vol. 18, pp. 36-43, 2000.
Tubaro, A., "The Artificial Bladder", Eur Urol., vol. 35, pp. 257-266, 1999 (Abstract).
Kenefick, N.J., et al., "Injectable Silicon Biomaterial for Faecal Incontinence Due to Internal Anal Sphincter Dysfunction", Gut., vol. 51, pp. 225-228, 2002.
Oberpenning et al., "De novo reconstitution of a functional mammalian urinary bladder by tissue engineering", Nature Biotecchnology, vol. 17, No. 2; Feb. 1, 1999; pp. 149-155.

* cited by examiner

Figure 1
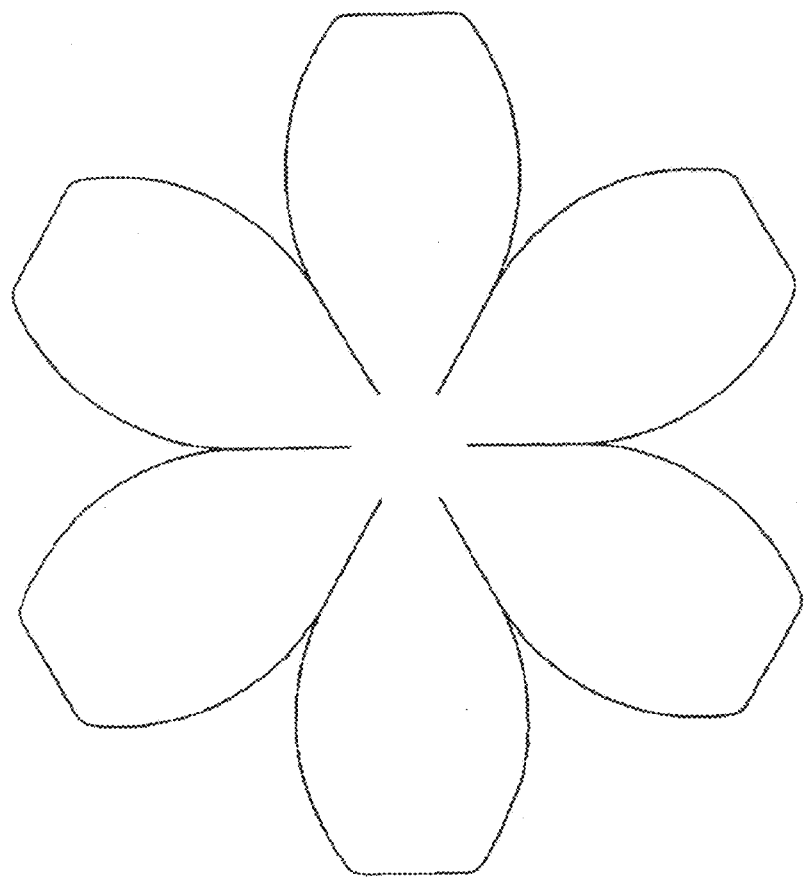
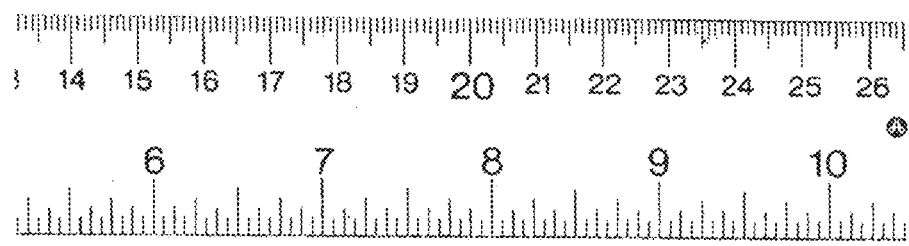

Figure 2
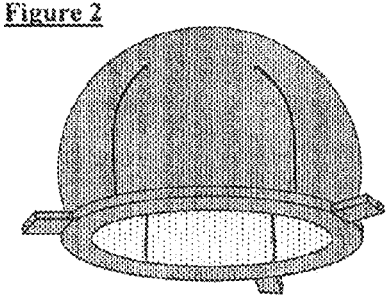
Construct with Flange (Seeded)
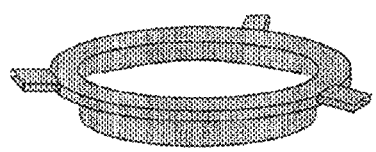
Flanged Collar (Unseeded)
Figure 3
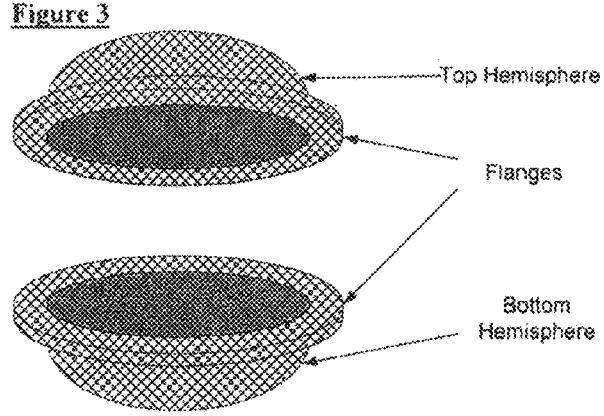
Top Hemisphere
Flanges
Bottom Hemisphere Hemispheres in place
to be joined Hollow construct after
joining and trimming
of flanges

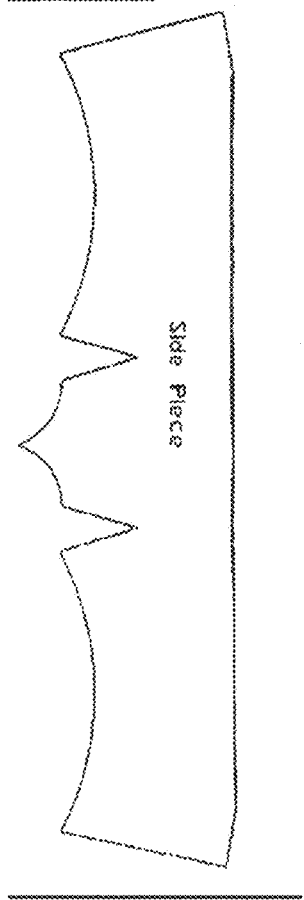

Figure 21
(A)
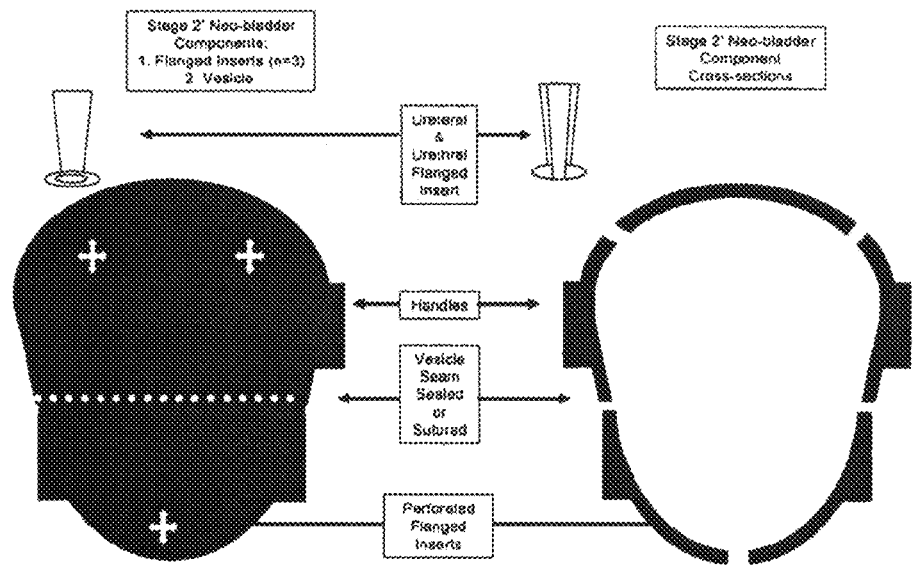
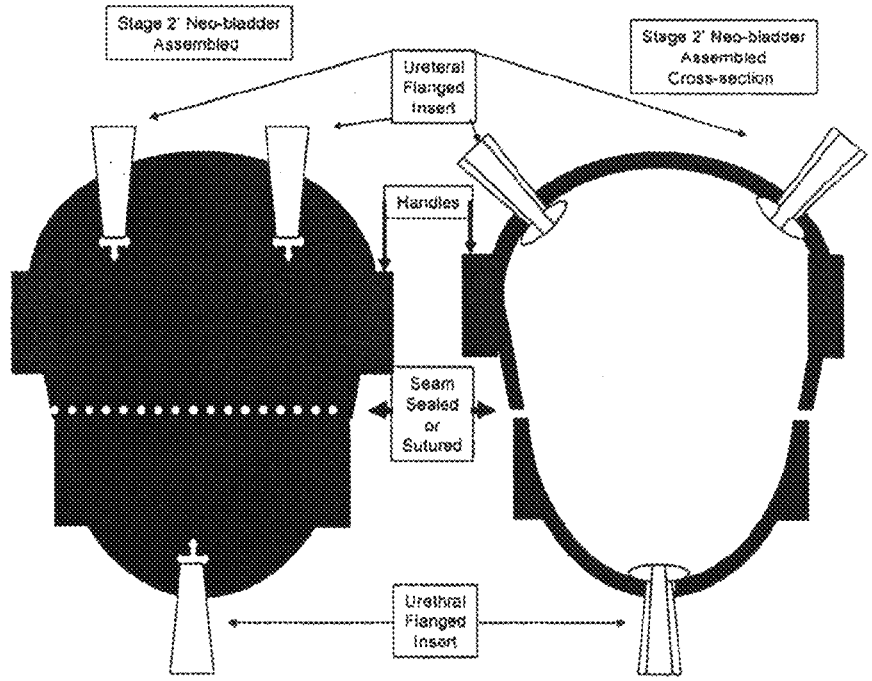

SCAFFOLDS FOR ORGAN RECONSTRUCTION AND AUGMENTATION

REFERENCE TO RELATED APPLICATIONS

This application claims priority under 35 U.S.C. §120 and is a continuation of U.S. patent application Ser. No. 11/706,081 filed Feb. 12, 2007 now U.S. Pat. No. 7,918,897, which claims priority under 35 U.S.C. §119(e) to U.S. Provisional Application Ser. No. 60/772,754, filed Feb. 10, 2006, the entire disclosures of which are incorporated herein by reference in their entirety.

FIELD OF THE INVENTION

The invention is directed to neo-organ constructs and methods for tissue and organ reconstruction, repair, augmentation and replacement and particularly to use of these neo-organ constructs in patients having a defect in urogenital tissues or organs or both, such as the bladder. The invention is directed also to methods and materials for attachment of vessels and other tubular elements to neo-organ constructs for tissue reconstruction, repair, augmentation and replacement.

BACKGROUND OF THE INVENTION

The medical community has directed considerable attention and effort to the substitution of defective organs with operationally effective replacements. The replacements have ranged from completely synthetic devices such as artificial hearts to completely natural organs from another mammalian donor. The field of heart transplants has been especially successful with the use of both synthetic hearts and natural hearts from living donors. Equal success has not been achieved in many other organ fields particularly in the field of bladder reconstruction.

The human urinary bladder is a musculomembranous sac, situated in the anterior part of the pelvic cavity, that serves as a reservoir for urine, which it receives through the ureters and discharges through the urethra. In a human the bladder is found in the pelvis behind the pelvic bone (pubic symphysis) and is above and posterior to a drainage tube, called the urethra, that exits to the outside of the body. The bladder, ureters, and urethra are all similarly structured in that they comprise muscular structures lined with a membrane comprising urothelial cells coated with mucus that is impermeable to the normal soluble substances of the urine. The trigone of the bladder, also called the trigonum vesicae, is a smooth triangular portion of the mucous membrane at the base of the bladder. The bladder tissue is elastic and compliant. That is, the bladder changes shape and size according to the amount of urine it contains. A bladder resembles a deflated balloon when empty but becomes somewhat pear-shaped and rises into the abdominal cavity when the amount of urine in it increases.

The bladder wall has three main layers of tissues: the mucosa, submucosa, and detrusor. The mucosa, comprising urothelial cells, is the innermost layer and is composed of transitional cell epithelium. The submucosa lies immediately beneath the mucosa and its basement membrane. It is composed of blood vessels which supply the mucosa with nutrients and the lymph nodes which aid in the removal of waste products. The detrusor is a layer of smooth muscle cells which expands to store urine and contracts to expel urine.

The urinary bladder is subject to numerous maladies and injuries which cause deterioration of the urinary bladder in patients. For example, bladder deterioration may result from infectious diseases, neoplasms and developmental abnormalities. Further, bladder deterioration may also occur as a result of trauma such as, for example, car accidents and sports injury.

Although a large number of bio-materials, including synthetic and naturally-derived polymers, have been employed for tissue reconstruction or augmentation (see, e.g., "Textbook of Tissue Engineering" Eds. Lanza, R., Langer, R., and Chick, W, ACM Press, Colorado (1996) and references cited therein), many materials have proven to be unsatisfactory for use in bladder reconstruction. For example, synthetic biomaterials such as polyvinyl and gelatin sponges, polytetrafluoroethylene (Teflon) felt, and silastic patches have been relatively unsuccessful, generally due to foreign body reactions (see, e.g., Kudish, H. G., J. Urol. 78:232 (1957); Ashkar, L. and Heller, E., J. Urol. 98:91 (1967); Kelami, A. et al., J. Urol. 104:693 (1970)). Other attempts have usually failed due to mechanical, structural, functional, or biocompatibility problems. Permanent synthetic materials have been associated with mechanical failure and calculus formation.

Naturally-derived materials such as lyophilized dura, deepithelialized bowel segments, and small intestinal submucosa (SIS) have also been proposed for bladder replacement (for a general review, see Mooney, D. et al., "Tissue Engineering: Urogenital System" in "Textbook of Tissue Engineering" Eds. Lanza, R., Langer, R., and Chick, W., ACM Press, Colorado (1996)). However, it has been reported that bladders augmented with dura, peritoneum, placenta and fascia contract over time (Kelami, A. et al., J. Urol. 105:518 (1971)). De-epithelized bowel segments demonstrated an adequate urothelial covering for use in bladder reconstruction, but difficulties remain with either mucosal regrowth, segment fibrosis, or both. It has been shown that de-epithelization of the intestinal segments may lead to mucosal regrowth, whereas removal of the mucosa and submucosa may lead to retraction of the intestinal segment (see, e.g., Atala, A., J. Urol. 156:338 (1996)).

Other problems have been reported with the use of certain gastrointestinal segments for bladder surgery including stone formation, increased mucus production, neoplasia, infection, metabolic disturbances, long term contracture and resorption. These attempts with natural or synthetic materials have shown that bladder tissue, with its specific muscular elastic properties and urothelial impermeability functions, cannot be easily replaced.

Due to the multiple complications associated with the use of gastrointestinal segments for bladder reconstruction, investigators have sought alternate solutions. Recent surgical approaches have relied on native urological tissue for reconstruction, including auto-augmentation and ureterocystoplasty. However, auto-augmentation has been associated with disappointing long-term results and ureterocystoplasty is limited to cases in which a dilated ureter is already present. A system of progressive dilation for ureters and bladders has been proposed, however, this has not yet been attempted clinically. Sero-muscular grafts and de-epithelialized bowel segments, either alone or over a native urothelium, have also been attempted. However, graft shrinkage and re-epithelialization of initially de-epithelialized bowel segments has been a recurring problem.

One significant limitation besetting bladder reconstruction is directly related to the availability of donor tissue. The limited availability of bladder tissue prohibits the frequent routine reconstruction of bladder using normal bladder tissue. The bladder tissue that is available, and considered usable, may itself include inherent imperfections and disease. For example, in a patient suffering from bladder cancer, the remaining bladder tissue may be contaminated with metastasis. Accordingly, the patient is predestined to less than perfect bladder function.

Accordingly, there exists a need for methods and devices for the reconstruction, repair, augmentation or replacement of organs or tissue structures in a patient in need of such treatment. In addition, there is a need for artificial organ constructs with improved biomechanical properties.

BRIEF SUMMARY OF THE INVENTION

Biocompatible synthetic or natural scaffolds are provided for the reconstruction, repair, augmentation or replacement of organs or tissue structures in a patient in need of such treatment.

The scaffolds are shaped to conform to at least a part of the organ or tissue structure and may be seeded with one or more cell populations. The seeded scaffolds are implanted into the patient at the site in need of treatment to form an organized organ or tissue structure. The scaffolds may be used to form organs or tissues, such as a bladder.

The constructs described herein for the reconstruction, repair, augmentation or replacement of laminarily organized luminal organs or tissue structures include an implantable, biocompatible, synthetic or natural polymeric matrix or scaffold having at least two separate surfaces and shaped to conform to at least a part of the luminal organ or tissue structure in need of the treatment, at least one receptacle or port adapted to receive a tubular vessel or insert; and at least one cell population deposited on or in a first surface of the polymeric matrix, a second surface of the polymeric matrix, or both, to form a construct of matrix plus cells, wherein the at least one cell population comprises at least one cell population that is substantially a muscle cell population. The muscle cell population is, e.g., a smooth muscle cell population. Optionally, a second cell population may be deposited on or in a first surface of the polymeric matrix, a second surface of the polymeric matrix, or both, wherein the second cell population comprises a urothelial cell population.

The constructs described herein for the reconstruction, repair, augmentation or replacement of laminarily organized luminal organs or tissue structures also comprise a first implantable, biocompatible, synthetic or natural polymeric matrix or scaffold having at least two separate surfaces, and a second implantable, biocompatible, synthetic or natural polymeric matrix or scaffold having at least two separate surfaces, which are adapted to mate to each other and shaped to conform to at least a part of the luminal organ or tissue structure in need of the treatment when mated. The first and second polymeric matrices may be formed from one integral unit subdivided into two or more distinct parts, or from two or more distinct parts, adapted to mate.

In some embodiments, the first and second polymeric matrices are symmetrical, while in other embodiments, the first and second polymeric matrices are asymmetrical. In one embodiment, the first polymeric matrix or scaffold has a hemispherical or quasi-hemispherical shape having a closed, domed end and an open, equatorial border, and the second polymeric matrix or scaffold is a collar adapted to mate with the equatorial border of the first polymeric matrix. In another embodiment, the first and second polymeric matrices are each hemispherical or quasi-hemispherical in shape, having a closed, domed end and an open, equatorial border. In yet another embodiment, the first and second polymeric matrices each comprise a circular or semi-circular base and at least 2 petals radially extending from each base. In this embodiment, the bases and petal shaped portions of the first and the second polymeric matrices are mated to create a hollow spherical or quasi-spherical matrix or scaffold such that a flanged longitudinal, elliptical opening is created on one side of the mated polymeric matrices, and a circular opening is created on the side opposite the longitudinal opening. In another embodiment, the first and second polymeric matrices are made from 3 parts comprising a top, a front and a sidepiece, adapted to mate. In this embodiment, the 3 distinct parts are mated using at least 3, preferably four vertical seams, thereby forming a crown shaped neo-bladder construct. The crown shaped constructs are preferably used alone as a device for organ repair or augmentation.

The first polymeric matrix or the second polymeric matrix, if any, or both, comprise at least one cell population deposited on or in a first surface of the first polymeric matrix, a first surface of the second polymeric matrix, or both, to form a construct of matrix or scaffold plus cells, wherein at least one cell population comprises substantially a muscle cell population. The muscle cell population is, e.g., a smooth muscle cell population. Optionally, a second cell population may be deposited on or in a second surface of the first polymeric matrix or a second surface of the second polymeric matrix, or both, wherein the second cell population comprises a urothelial cell population. Additionally, the first polymeric matrix, the second polymeric matrix, or both, may contain at least one receptacle or port adapted to receive a tubular vessel or insert where the connection of the construct to a native vessel or tube is necessary.

The biocompatible material used for these constructs is, for example, biodegradable. In some constructs, the biocompatible material is polyglycolic acid. The vessels or inserts are themselves, for example, cylindrical or tubular shaped polymer matrices, each having at least one flange located at a first end of the cylindrical polymer. The vessels or inserts are, preferably, composed of the same biocompatible material as the first or second polymeric matrices described above. In some embodiments, the vessel or insert also contains a washer adapted to fit around the cylindrical or tubular vessel or insert polymer matrix. For example, the washer is a hydrogel. The cylindrical or tubular vessel or insert may optionally contain a washer. The washer may be hydrogel. Additionally, the cylindrical or tubular insert may be self-stabilizing.

These constructs are used to treat, repair, augment or replace luminal organ or tissue structures such as genitourinary organs, including for example, the urinary bladder, ureters and urethra. For example, the luminal organ or tissue structure is a bladder or bladder segment, and the polymeric matrix or scaffold has smooth muscle cells deposited on a surface of the matrix.

In one embodiment, the methods described herein for the reconstruction, repair, augmentation or replacement of laminarily organized luminal organs or tissue structures in a patient in need of such treatment include the following steps: providing a biocompatible synthetic or natural polymeric matrix or scaffold shaped to conform to at least a part of the luminal organ or tissue structure in need of the treatment; depositing at least a first cell population on or in a first surface of the polymeric matrix or a second surface of the polymeric matrix or both, the first cell population being substantially a muscle cell population; and implanting the shaped polymeric matrix-cell construct into the patient at the site of the treatment for the regeneration of a luminal organ or tissue structure. Optionally, the polymeric matrix or scaffold contains at least one receptacle or port adapted to receive a tubular or cylindrical vessel or insert. Optionally, the methods described herein further include the step of depositing a second cell population on or in a first surface of the polymeric matrix or a second surface of the polymeric matrix or both, wherein the second cell population comprises a urothelial cell population.

In another embodiment, the methods described herein for the reconstruction, repair, augmentation or replacement of laminarily organized luminal organs or tissue structures in a patient in need of such treatment include the following steps: providing a first implantable, biocompatible, synthetic or natural polymeric matrix or scaffold having at least two separate surfaces, and a second implantable, biocompatible, synthetic or natural polymeric matrix or scaffold having at least two separate surfaces, which are adapted to mate to each other and shaped to conform to at least a part of the luminal organ or tissue structure in need of the treatment when mated; depositing at least a first cell population on or in a first surface of the first polymeric matrix or a first surface of the second polymeric matrix, or both, the first cell population being substantially a muscle cell population; and implanting the shaped polymeric matrix or scaffold cell construct into the patient at the site of the treatment for the regeneration of a luminal organ or tissue structure. Optionally, the first polymeric matrix or the second polymeric matrix, or both, contain at least one receptacle or port adapted to receive a cylindrical or tubular vessel or port. Optionally, the methods described herein further include the step of depositing a second cell population on or in a first surface of the first polymeric matrix or a second surface of the second polymeric matrix, or both, wherein the second cell population comprises a urothelial cell population.

In another embodiment, more than two separate biocompatible polymeric matrices, one or more of which may be seeded with one or more cell populations and one or more of which may contain at least one receptacle or port adapted to receive a cylindrical or tubular vessel or insert may be provided and implanted in a patient at a site of the treatment for the regeneration of a luminal organ or tissue structure.

The biocompatible material used in these methods is, for example, biodegradable. In some methods, the biocompatible material is polyglycolic acid. The vessels or inserts are, for example, cylindrical or tubular shaped polymer matrices having at least one flange located at a first end of the cylindrical or tubular matrix. The vessels or inserts are, preferably, composed of the same biocompatible material as the matrices into which they are inserted. In some embodiments, the vessel or insert also contains a washer adapted to fit around the cylindrical polymer. For example, the washer is a hydrogel.

These methods are used to treat, repair, replace or augment luminal organ or tissue structures such as genitourinary organs, including for example, the urinary bladder, ureters and urethra. For example, the luminal organ or tissue structure is a bladder or bladder segment, and the polymeric matrix or scaffold (or matrices) have smooth muscle cells deposited on a surface thereof. These methods are also used to treat, repair, replace or augment other organs and tissue structures, such as, for example, kidneys, blood vessels and reproductive organs such as the uterus.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIG. 1 is an illustration depicting a template for a multi-petal-shaped neo-organ matrix or scaffold. The edges of the petals are mated to form a quasi-spherical shaped hollow matrix.

FIG. 2 is an illustration depicting a two-part neo-organ matrix or scaffold for organ augmentation that includes a dome-shaped piece with a flanged equatorial border having flaps, this first piece being seeded with cells, and a second piece comprising a ring with a flanged collar having flaps, the flanged collar designed to mate with the flanged equatorial border of the dome piece.

FIG. 3 is an illustration depicting a two-part neo-organ matrix or scaffold for organ replacement, each part having a hemispherical or quasi-hemispherical shape and each with a flanged equatorial border for mating the two parts.

FIGS. 11A-11C is an illustration depicting a three-part template design for constructing a quasi-hemispherical crown shaped neo-organ matrix or scaffold. FIG. 11A depicts the top piece of the crown shaped scaffold; FIG. 11B depicts the front piece of the crown shaped scaffold; FIG. 11C depicts the side piece of the crown shaped scaffold.

FIG. 12A is a side view of the crown shaped scaffold; FIG. 12B depicts the front view of the crown shaped scaffold; FIG. 12C depicts a top view of the crown shaped scaffold; FIG. 12D depicts the bottom view of the crown shaped scaffold.

FIG. 17 depicts a shipping container with a screw-cap lid for packing and transporting cell-seeded neo-organ constructs.

FIG. 18 depicts an aerial view of the shipping container depicted in FIG. 17, without the screw-cap lid, showing an inner basket supporting a cell-seeded neo-organ construct.

FIG. 19 depicts the inner support basket shown in FIG. 18 with a cell-seeded neo-20 organ construct inside the basket.

FIG. 20 depicts a temperature controlled, insulated box used to ship the neo-organ construct shipping container depicted in FIG. 17.

FIGS. 21A-21D are a series of illustrations depicting a joined two-part, hollow neo-organ polymeric matrix or scaffold for organ replacement, with receptacles or ports for the attachment of tubular vessels or inserts such as the ureters and the urethra. Panels A and C provide a solid view of the assembled neo-organ construct for organ replacement, while Panels B and D provide a cross-sectional view of the assembled construct. Each of these panels also depicts the polymeric flanged tubular vessel or insert matrices, which are to be inserted into the receptacles or ports joined two-part hollow matrix.

FIG. 29A is an illustration of bladder augmentation surgery using a previous neo-organ augmentation construct design while FIG. 29B is an illustration of bladder augmentation using a modified neo-organ construct design with flaps and an outer rim.

DETAILED DESCRIPTION OF THE INVENTION

Figure 4:
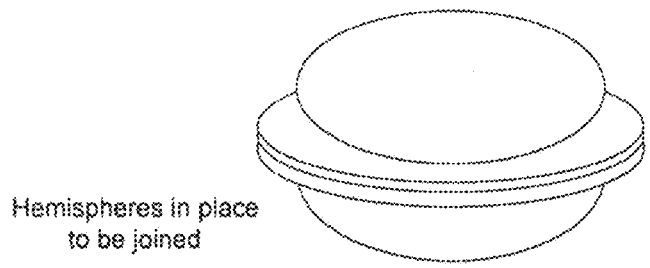
FIG. 4 is an illustration depicting the two-part neo-organ matrix or scaffold portions of the two-part scaffold shown in FIG. 3 with flanges ready to be joined.

Constructs and methods useful in the reconstruction, repair, augmentation or replacement of organs or tissues structures are provided.

In its broadest form, the constructs and methods of the present invention are useful in the reconstruction, repair, augmentation or replacement of organs or tissues structures that comprise multilayer cellular organization and particularly those organs or tissue structures that are luminal in nature. More particularly, the present invention provides constructs and methods that facilitate the reconstruction, repair, augmentation or replacement of shaped hollow organs or tissue structures that exhibit a laminar segregation of different cell types and that have a need to retain a general luminal shape. Luminal organs or tissue structures that contain a smooth muscle cell (SMC) layer to impart compliant or contractible properties to the organ or structure are particularly well suited to the constructs and methods of the present invention.

In an example of one preferred embodiment of the invention, the luminal organ is the bladder, which has an inner layer of a first cell population that comprises urothelial cells and an outer layer of a second cell population that comprises smooth muscle cells. This organization is also present in other genitourinary organs and tissue structures such as the ureters and urethra. Laminarily organized organs or tissues refer to any organ or tissue made up of, or arranged in laminae including ductal tissue. Other suitable laminarily organized luminal organs, tissue structure, or ductal tissues to which the present invention is directed include vas deferens, fallopian tubes, lacrimal ducts, trachea, stomach, intestines, vasculature, biliary duct, ductus ejaculatorius, ductus epididymidis, ductus parotideus, and surgically created shunts. Other suitable organs and tissue structures include, for example, kidneys, blood vessels and reproductive organs such as the uterus.

The neo-organ constructs and methods of the present invention comprise a biocompatible synthetic or natural polymeric matrix or scaffold, and one or more cell populations seeded on one or more surfaces of the matrix or scaffold. The method of the present invention in its broadest aspect encompasses as a first step providing a biocompatible synthetic or natural polymeric matrix or scaffold that is shaped to conform to its use as a part or all of the luminal organ or tissue structure to be repaired, reconstructed, augmented or replaced. Hereinafter, the terms matrix and scaffold may be used interchangeably. A biocompatible material is any substance not having toxic or injurious effects on biological function. The shaped matrix or scaffold is preferably porous to allow for cell deposition both on and in the pores of the matrix. The shaped matrix or scaffold may then be contacted with one or more cell populations to seed the cell populations on or into (or both) the matrix or scaffold. The cell-seeded matrix scaffold (i.e., the construct) is then implanted in the body of the recipient where the construct facilitates the regeneration of neo-organs or tissue structures. The constructs may be used to reconstruct, repair, augment or replace any organ, and may especially be utilized in patients having a defect in urogenital tissues such as the bladder.

In a preferred embodiment, the materials and methods of the invention are useful for the reconstruction, replacement or augmentation of bladder tissue. Thus, the invention provides treatments for such conditions as neurogenic bladder, bladder exstrophy, bladder volume insufficiency, bladder non-compliance, reconstruction of bladder following partial or total cystectomy, repair of bladders damaged by trauma, and the like.

One issue that can face the surgeon during the implantation of a neo-organ construct or neo-vessel construct, such as a bladder, kidney or blood vessel, is the attachment of vessels, such as the urethra, ureters, and renal blood vessels. Currently, one method to achieve this is for the resected end of the urethra or ureter to be fed through a hole in the wall of the neo-bladder construct and splatulated and sutured into the interior of the construct. Limitations with this method include extended working time during which the neo-bladder construct is out of medium (which negatively impacts the viability of the cells contains on the construct), cumbersomeness of working with neo-bladder construct during splatulation and suturing with resulting damage to the neo-bladder construct, and the requirement for the surgeon to be suturing in the tight spaces in the bottom of the bladder "bowl".

The constructs and methods described herein are designed to improve the ease with, and reduce the surgical time in which vessels and other tubular structures, such as the urethra and ureter, are surgically connected to a neo-organ construct such as a neo-bladder construct. The current invention provides for the use of a flanged tubular matrix to address this issue. The methods described herein are also used to improve the ease with which vessels and other tubular structures, such as blood vessels, are surgically connected to a neo-organ, to a neo-vessel structure or to another blood vessel. According to one method, the neo-organ construct is a neo-bladder construct, and the urethra is first attached to a tubular element which is flanged at one end, referred to herein as an insert, then the flanged end of the insert is placed into the interior of the neo-bladder. In contrast to current methods, the insert is not initially attached to the neo-bladder construct. Insert design variations alleviating the need for suturing to the neo-bladder construct, and the use of a hydrogel to facilitate seating of the insert, are also disclosed. Matrix or scaffold design variations, include tabs on the scaffold to ease positioning during implantation, a flanged collar to help attach the cut edge of the native bladder trigone to the flanged cell seeded neo-bladder construct, and an approach of forming two-part neo-organ constructs with a geometry that allows for easier access to elements inside the constructs prior to joining them, and an approach to join two halves of neo-organs, are also presented.

While reference is made herein to reconstructions, replacements or augmentation of the bladder and methods of attaching vessels such as the urethra or ureter to a neo-bladder construct, it will be understood that the methods and materials described herein are useful for tissue reconstruction, replacement or augmentation of a variety of tissues and organs in a subject. Thus, for example, organs or tissues such as bladder, ureter, urethra, renal pelvis, and the like, can be augmented or repaired with polymeric matrixes seeded with cells. The materials and methods of the invention further can be applied to the reconstruction, replacement or augmentation of vascular tissue (see, e.g., Zdrahala, R. J., J Biomater. Appl. 10 (4): 309-29 (1996)), intestinal tissues, stomach (see, e.g., Laurencin, C. T. et al., J Biomed Mater. Res. 30 (2): 133-8 1996), and the like. The patient to be treated may be of any species of mammals such as a dog, cat, pig, horse, cow, or human, in need of reconstruction, repair, replacement or augmentation of a tissue.

Neo-Organ Matrix or Scaffolds

Biocompatible material and especially biodegradable material is the preferred material for the construction of the matrix.

Biocompatible refers to materials which do not have toxic or injurious effects on biological functions. Biodegradable refers to material that can be absorbed or degraded in a patient's body. Representative materials for forming the biodegradable matrix or scaffold include natural or synthetic polymers, such as, for example, collagen, poly(alpha esters) such as poly(lactic acid) and poly(glycolic acid), polyorthoesters and polyanhydrides and their copolymers, which degrade by hydrolysis at a controlled rate and are reabsorbed. These materials provide the maximum control of degradability, manageability, size and configuration. Preferred biodegradable polymer material includes polyglycolic acid and polyglactin, developed as absorbable synthetic material. Polyglycolic acid and polyglactin fibers may be used as supplied by the manufacturer. Other biodegradable materials include cellulose ether, cellulose, cellulosic ester, fluorinated polyethylene, phenolic, poly-4-methylpentene, polyacrylonitrile, polyamide, polyamideimide, polyacrylate, polybenzoxazole, polycarbonate, polycyanoarylether, polyester, polyestercarbonate, polyether, polyetheretherketone, polyetherimide, polyetherketone, polyethersulfone, polyethylene, polyfluoroolefin, polyimide, polyolefin, polyoxadiazole, polyphenylene oxide, polyphenylene sulfide, polypropylene, polystyrene, polycaprolactone, polysulfide, polysulfone, polytetrafluoroethylene, polythioether, polytriazole, polyurethane, polyvinyl, polyvinylidene fluoride, regenerated cellulose, silicone, urea-formaldehyde, or copolymers or physical blends of these materials. The material may be impregnated with suitable antimicrobial agents and may be colored by a color additive to improve visibility and to aid in surgical procedures.

Other biocompatible materials include synthetic suture material manufactured by Ethicon Co. (Ethicon Co., Somerville, N.J.), such as MONOCRYL® (copolymer of glycolide and epsilon-caprolactone), VICRYL® or Polyglactin 910 (copolymer of lactide and glycolide coated with Polyglactin 370 and calcium stearate), and PANACRYL® (copolymer of lactide and glycolide coated with a polymer of caprolactone and glycolide). (Craig P. H., Williams J. A., Davis K. W., et al.: A Biological Comparison of Polyglactin 910 and Polyglycolic Acid Synthetic Absorbable Sutures. Surg. 141; 1010, (1975)) and polyglycolic acid. These materials can be used as supplied by the manufacturer.

In yet another embodiment, the matrix or scaffold can be created using parts of a natural decellularized organ. Biostructures, or parts of organs can be decellularized by removing the entire cellular and tissue content from the organ. The decellularization process comprises a series of sequential extractions. One key feature of this extraction process is that harsh extraction that may disturb or destroy the complex infra-structure of the biostructure, be avoided. The first step involves removal of cellular debris and solubilization of the cell membrane. This is followed by solubilization of the nuclear cytoplasmic components and the nuclear components.

Preferably, the biostructure, e.g., part of an organ is decellularized by removing the cell membrane and cellular debris surrounding the part of the organ using gentle mechanical disruption methods. The gentle mechanical disruption methods must be sufficient to disrupt the cellular membrane. However, the process of decellularization should avoid damage or disturbance of the biostructure's complex infra-structure. Gentle mechanical disruption methods include scraping the surface of the organ part, agitating the organ part, or stirring the organ in a suitable volume of fluid, e.g., distilled water. In one preferred embodiment, the gentle mechanical disruption method includes stirring the organ part in a suitable volume of distilled water until the cell membrane is disrupted and the cellular debris has been removed from the organ.

After the cell membrane has been removed, the nuclear and cytoplasmic components of the biostructure are removed. This can be performed by solubilizing the cellular and nuclear components without disrupting the infra-structure. To solubilize the nuclear components, non-ionic detergents or surfactants may be used. Examples of nonionic detergents or surfactants include, but are not limited to, the Triton series, available from Rohm and Haas of Philadelphia, Pa., which includes Triton X-100, Triton N-101, Triton X-114, Triton X-405, Triton X-705, and Triton DF-16, available commercially from many vendors; the Tween series, such as monolaurate (Tween 20), monopalmitate (Tween 40), monooleate (Tween 80), and polyoxethylene-23-lauryl ether (Brij. 35), polyoxyethylene ether W-1 (Polyox), and the like, sodium cholate, deoxycholates, CHAPS, saponin, n-Decyl-D-glucopuranoside, n-heptyl-D-glucopyranoside, n-Octyl-D-glucopyranoside and Nonidet P-40.

One skilled in the art will appreciate that a description of compounds belonging to the foregoing classifications, and vendors may be commercially obtained and may be found in "Chemical Classification, Emulsifiers and Detergents", McCutcheon's, Emulsifiers and Detergents, 1986, North American and International Editions, McCutcheon Division, MC Publishing Co., Glen Rock, N.J., U.S.A. and Judith Neugebauer, A Guide to the Properties and Uses of Detergents in Biology and Biochemistry, Calbiochem. R., Hoechst Celanese Corp., 1987. In one preferred embodiment, the nonionic surfactant is the Triton. series, preferably, Triton X-100.

The concentration of the non-ionic detergent may be altered depending on the type of biostructure being decellularized. For example, for delicate tissues, e.g., blood vessels, the concentration of the detergent should be decreased. Preferred concentration ranges of nonionic detergent can be from about 0.001 to about 2.0% (w/v). More preferably, about 0.05 to about 1.0% (w/v). Even more preferably, about, 0.1% (w/v) to about 0.8% (w/v). Preferred concentrations of these range from about 0.001 to about 0.2% (w/v), with about 0.05 to about 0.1% (w/v) particular preferred.

The cytoskeletal component, which includes the dense cytoplasmic filament networks, intercellular complexes and apical microcellular structures, may be solubilized using alkaline solution, such as, ammonium hydroxide. Other alkaline solution consisting of ammonium salts or their derivatives may also be used to solubilize the cytoskeletal components. Examples of other suitable ammonium solutions include ammonium sulphate, ammonium acetate and ammonium hydroxide. In a preferred embodiment, ammonium hydroxide is used.

The concentration of the alkaline solutions, e.g., ammonium hydroxide, may be altered depending on the type of biostructure being decellularized. For example, for delicate tissues, e.g., blood vessels, the concentration of the detergent should be decreased. Preferred concentrations ranges can be from about 0.001 to about 2.0% (w/v). More preferably, about 0.005 to about 0.1% (w/v). Even more preferably, about, 0.01% (w/v) to about 0.08% (w/v). The decellularized, lyophilized structure may be stored at a suitable temperature until required for use. Prior to use, the decellularized structure can be equilibrated in suitable isotonic buffer or cell culture medium. Suitable buffers include, but are not limited to, phosphate buffered saline (PBS), saline, MOPS, HEPES, Hank's Balanced Salt Solution, and the like. Suitable cell culture medium includes, but is not limited to, RPMI 1640, Fisher's, Iscove's, McCoy's, Dulbecco's medium, and the like.

Still other biocompatible materials that may be used include stainless steel, titanium, silicone, gold and silastic.

The biocompatible polymer may be shaped using methods such as, for example, solvent casting, compression molding, filament drawing, meshing, leaching, weaving and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the construct. Next a solvent is used to dissolve away one of the components, resulting in pore formation. (See Mikos, U.S. Pat. No. 5,514,378, hereby incorporated by reference.) In nucleation, thin films in the shape of a RUG are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a structure with uniform pore sizes. Coating refers to coating or permeating a polymeric structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a polymeric matrix or scaffold may be weaved, compression molded and glued together. Furthermore different polymeric materials shaped by different processes may be joined together to form a composite shape. The composite shape may be a laminar structure. For example, a polymeric matrix or scaffold may be attached to one or more polymeric matrixes to form a multilayer polymeric matrix or scaffold structure. The attachment may be performed by gluing with a liquid polymer or by suturing. In addition, the polymeric matrix or scaffold may be formed as a solid block and shaped by laser or other standard machining techniques to its desired final form. Laser shaping refers to the process of removing materials using a laser.

The polymeric matrix or scaffold can be reinforced. For example, reinforcing materials may be added during the formation of a synthetic matrix or scaffold or attached to the natural or synthetic matrix prior to implantation. Representative materials for forming the reinforcement include natural or synthetic polymers, such as, for example, collagen, poly (alpha esters) such as poly(lactic acid), poly(glycolic acid), polyorthoesters and polyanhydrides and their copolymers, which degraded by hydrolysis at a controlled rate and are reabsorbed. These materials provide the maximum control of degradability, manageability, size and configuration.

The biodegradable polymers can be characterized with respect to mechanical properties, such as tensile strength using an Instron tester, for polymer molecular weight by gel permeation chromatography (GPC), glass, transition temperature by differential scanning calorimetry (DSC) and bond structure by infrared (IR) spectroscopy; with respect to toxicology by initial screening tests involving Ames assays and in vitro teratogenicity assays and implantation studies in animals for immunogenicity, inflammation, release and degradation studies. In vitro cell attachment and viability can be assessed using scanning electron microscopy, histology and quantitative assessment with radioisotopes. The biodegradable material may also be characterized with respect to the amount of time necessary for the material to degrade when implanted in a patient. By varying the construction, such as, for example, the thickness and mesh size, the biodegradable material may substantially biodegrade between about 2 years or about 2 months, preferably between about 18 months and about 4 months, most preferably between about 15 months and about 8 months and most preferably between about 12 months and about 10 months. If necessary, the biodegradable material may be constructed so as not to degrade substantially within about 3 years, or about 4 years or about five or more years.

The polymeric matrix or scaffold may be fabricated with controlled pore structure as described above. The size of the pores may be used to determine the cell distribution. For example, the pores on the polymeric matrix or scaffold may be large to enable cells to migrate from one surface to the opposite surface. Alternatively, the pores may be small such that there is fluid communication between the two sides of the polymeric matrix or scaffold but cells cannot pass through. Suitable pore size to accomplish this objective may be about 0.04 micron to about 10 microns in diameter, preferably between about 0.4 micron to about 4 microns in diameter. In some embodiments, the surface of the polymeric matrix or scaffold may comprise pores sufficiently large to allow attachment and migration of a first population of cells into the pores. The pore size may be reduced in the interior of the polymeric matrix or scaffold to prevent cells from migrating from one side of the polymeric matrix or scaffold to the opposite side. On the opposite side of the polymeric matrix, the pores may again enlarge to allow the attachment and establishment of a second population of cells. Because of the reduced pore size in the interior of the polymeric matrix, the first cell population and the second cell population initially cannot mix. One embodiment of a polymeric matrix or scaffold with reduced pore size is a laminated structure of a small pore material sandwiched between two large pore material. Alternatively, a large pore material laminated to a small pore material may also allow cells to establish growth on both sides without any intermixing of cells. Polycarbonate membranes are especially suitable because they can be fabricated in very controlled pore sizes such as, for example, about 0.01 microns, about 0.05 micron, about 0.1 micron, about 0.2 micron, about 0.45 micron, about 0.6 micron, about 1.0 micron, about 2.0 microns and about 4.0 microns. At the submicron level the polymeric matrix or scaffold may be impermeable to bacteria, viruses and other microbes.

The following characteristics or criteria, among others, are taken into account in the design of each discrete matrix, or part thereof: (i) shape, (ii) strength, (iii) stiffness and rigidity, and (iv) suturability (the degree to which the matrix, or part thereof, is readily sutured or otherwise attached to adjacent tissue). As used herein, the stiffness of a given matrix or scaffold is defined by the modulus of elasticity, a coefficient expressing the ratio between stress per unit area acting to deform the scaffold and the amount of deformation that results from it. (See e.g., Handbook of Biomaterials evaluation, Scientific, Technical, and Clinical Testing of Implant Materials, 2nd edition, edited by Andreas F. von Recum, (1999); Ratner, et al., Biomaterials Science: An Introduction to Materials in Medicine, Academic Press (1996)). The rigidity of a scaffold refers to the degree of flexibility (or lack thereof) exhibited by a given scaffold.

Each of these criteria is a variable that can be changed (through, among other things, the choice of material and the manufacturing process) to allow the matrix, or part thereof to best placed and modified to address the medical indication and the physiological function for which it is intended. For example, the material comprising the matrix or scaffold for bladder replacement, reconstruction and/or augmentation must be sufficiently strong to support sutures without tearing, while being sufficient compliant so as to accommodate fluctuating volumes of urine.

Optimally, the matrix or scaffold should be shaped such that after its biodegradation, the resulting reconstructed bladder is collapsible when empty in a fashion similar to a natural bladder and the ureters will not be obstructed while the urinary catheter has been removed from the tissue engineered bladder without leaving a leak point from the dome. The bioengineered bladder construct can be produced as one piece or each part can be individually produced or combinations of the sections can be produced as specific parts. Each specific matrix or scaffold part may be produced to have a specific function. Otherwise specific parts may be produced for manufacturing ease. Specific parts may be constructed of specific materials and may be designed to deliver specific properties. Specific part properties may include tensile strength similar to the native tissue (e.g. ureters) of 0.5 to 1.5 $MPa^2$ and an ultimate elongation of 30 to 100% or the tensile strength may range from 0.5 to 28 $MPa^2$, ultimate elongations may range from 10-200% and compression strength may be <12.

A mesh-like structure formed of fibers, which may be round, scalloped, flattened, star shaped, solitary or entwined with other fibers is preferred. The use of branching fibers is based upon the same principles which nature has used to solve the problem of increasing surface area proportionate to volume increases. All multicellular organisms utilize this repeating branching structure. Branching systems represent communication networks between organs, as well as the functional units of individual organs. Seeding and implanting this configuration with cells allows implantation of large numbers of cells, each of which is exposed to the environment of the host, providing for free exchange of nutrients and waste while neovascularization is achieved. The polymeric matrix or scaffold may be made flexible or rigid, depending on the desired final form, structure and function.

In one preferred embodiment, the polymeric matrix or scaffold is formed with a polyglycolic acid with an average fiber diameter of 15 μm and configured into a bladder shaped mold using 4-0 polyglactin 910 sutures. The resulting structure is coated with a liquefied copolymer, such as, for example, pol-DL-lactide-co-glycolide 50:50, 80 milligram per milliliter methylene chloride, in order to achieve adequate mechanical characteristics and to set its shape.

Polymeric matrixes can be treated with additives or drugs prior to implantation (before or after the polymeric matrix or scaffold is seeded with cells, if the optional seeded cells are employed), e.g., to promote the regeneration of new tissue after implantation. Thus, for example, growth factors, cytokines, extracellular matrix or scaffold components, and other bioactive materials can be added to the polymeric matrix or scaffold to promote graft healing and regeneration of new tissue. Such additives will in general be selected according to the tissue or organ being reconstructed, replaced or augmented, to ensure that appropriate new tissue is formed in the engrafted organ or tissue (for examples of such additives for use in promoting bone healing, see, e.g., Kirker-Head, C. A. Vet. Surg. 24 (5): 408-19 (1995)). For example, when polymeric matrices (optionally seeded with endothelial cells) are used to augment vascular tissue, vascular endothelial growth factor (VEGF), (see, e.g., U.S. Pat. No. 5,654,273) can be employed to promote the regeneration of new vascular tissue. Growth factors and other additives (e.g., epidermal growth factor (EGF), heparin-binding epidermal-like growth factor (HBGF), fibroblast growth factor (FGF), cytokines, genes, proteins, and the like) can be added in amounts in excess of any amount of such growth factors (if any) which may be produced by the cells seeded on the polymeric matrix, if added cells are employed. Such additives are preferably provided in an amount sufficient to promote the regeneration of new tissue of a type appropriate to the tissue or organ, which is to be repaired, replaced or augmented (e.g., by causing or accelerating infiltration of host cells into the graft). Other useful additives include antibacterial agents such as antibiotics.

One preferred supporting matrix or scaffold is composed of crossing filaments which can allow cell survival by diffusion of nutrients across short distances once the cell support is implanted. The cell support matrix or scaffold becomes vascularized in concert with expansion of the cell mass following implantation.

The building of three-dimensional structure constructs in vitro, prior to implantation, facilitates the eventual terminal differentiation of the cells after implantation in vivo, and minimizes the risk of an inflammatory response towards the matrix, thus avoiding graft contracture and shrinkage.

The polymeric matrix or scaffold may be sterilized using any known method before use. The method used depend on the material used in the polymeric matrix. Examples of sterilization methods include steam, dry heat, radiation, gases such as ethylene oxide, gas and boiling.

Method for Forming Neo Organ Matrices or Scaffolds

The biocompatible scaffold may be shaped using methods such as, for example, solvent casting, compression molding, filament drawing, meshing, leaching, weaving, foaming, electrospinning and coating. In solvent casting, a solution of one or more polymers in an appropriate solvent, such as methylene chloride, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the artificial organ. Next a solvent is used to dissolve away one of the components, resulting in pore formation. (See U.S. Pat. No. 5,514,378 to Mikos).

In nucleation, thin films in the shape of an artificial organ are exposed to radioactive fission products that create tracks of radiation damaged material. Next the polycarbonate sheets are etched with acid or base, turning the tracks of radiation-damaged material into pores. Finally, a laser may be used to shape and burn individual holes through many materials to form a scaffold structure with uniform pore sizes. Coating refers to coating or permeating a structure with a material such as, for example liquefied copolymers (poly-DL-lactide co-glycolide 50:50 80 mg/ml methylene chloride) to alter its mechanical properties. Coating may be performed in one layer, or multiple layers until the desired mechanical properties are achieved. These shaping techniques may be employed in combination, for example, a scaffold may be weaved, compression molded and glued together. Furthermore different materials shaped by different processes may be joined together to form a composite shape. The composite shape may be a laminar structure. For example, a matrix or scaffold may be attached to one or more matrices to form a multilayer scaffold structure. The attachment may be performed by gluing with a liquid polymer or by suturing. In addition, the matrix or scaffold may be formed as a solid block and shaped by laser or other standard machining techniques to its desired final form. Laser shaping refers to the process of removing materials using a laser.

The scaffold may be shaped into any number of desirable configurations to satisfy any number of overall system, geometry or space restrictions. For example, in the use of the scaffold for bladder, urethra, valve, or blood vessel reconstruction, the matrix or scaffold may be shaped to conform to the dimensions and shapes of the whole or a part of the tissue. Naturally, the scaffold may be shaped in different sizes and shapes to conform to the organs of differently sized patients. For bladders, the scaffold should be shaped such that after its biodegradation, the resulting reconstructed bladder may be collapsible when empty in a fashion similar to a natural bladder. The matrix or scaffold may also be shaped in other fashions to accommodate the special needs of the patient.

Cells for Organ Reconstruction

In one embodiment, the scaffolds are seeded with one or more populations of cells to form an artificial organ construct. The artificial organ construct can be autologous, where the cell populations are derived from the subject's own tissue, or allogenic, where the cell populations are derived from another subject within the same species as the patient. The artificial organ construct can also be xenogenic; where the different cell populations are derived form a mammalian species that is different from the subject. For example the cells can be derived from organs of mammals such as humans, monkeys, dogs, cats, mice, rats, cows, horses, pigs, goats and sheep.

The process for isolating cell is described generally herein, and specific procedures are presented in the examples provided below. Cells can be isolated from a number of sources, including, for example, biopsies from living subjects and whole-organ recover from cadavers. The isolated cells are preferably autologous cells, obtained by biopsy from the subject intended to be the recipient. For example, a biopsy of skeletal muscle from the arm, forearm, or lower extremities, or smooth muscle from the area treated with local anesthetic with a small amount of lidocaine injected subcutaneously, and expanded in culture. The biopsy can be obtained using a biopsy needle, a rapid action needle which makes the procedure quick and simple. The small biopsy core of either skeletal or smooth muscle can then be expanded and cultured, as described by Atala, et al., (1992) J. Urol. 148, 658-62; Atala, et al. (1993) J. Urol. 150: 608-12. Cells from relatives or other donors of the same species can also be used with appropriate immunosuppression.

Methods for the isolation and culture of cells are discussed in Fauza et al. (1998) J. Ped. Surg. 33, 7-12, incorporated herein by reference. Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption can also be accomplished by a number of methods including, but not limited to, scraping the surface of the organ, the use of grinders, blenders, sieves, homogenizers, pressure cells, or insonicators. For a review of tissue disaggregation techniques, see Freshney, (1987), Culture of Animal Cells. A Manual of Basic Technique, 2d Ed., A. R. Liss, Inc., New York, Ch. 9, pp. 107-126.

Preferred cell types include, but are not limited to, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage. In some cases, it may also be desirable to include nerve cells.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting. For a review of clonal selection and cell separation techniques, see Freshney, (1987), Culture of Animal Cells. A Manual of Basic Techniques, 2d Ed., A. R. Liss, Inc., New York, Ch. 11 and 12, pp. 137-168. For example, one cell type may be enriched by magnetic-activated and fluorescence-activated cell sorting, and other cell types may be reduced for collection of a specific cell type.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used for organ reconstruction.

Isolated cells can be cultured in vitro to increase the number of cells available for coating the biocompatible scaffold. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the biocompatible scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery.

Isolated cells can be normal or genetically engineered to provide additional or normal function. Methods for genetically engineering cells with retroviral vectors, polyethylene glycol, or other methods known to those skilled in the art can be used. These include using expression vectors which transport and express nucleic acid molecules in the cells. (See Goeddel; Gene Expression Technology: Methods in Enzymology 185, Academic Press, San Diego, Calif. (1990).

Vector DNA is introduced into prokaryotic or cells via conventional transformation or transfection techniques. Suitable methods for transforming or transfecting host cells can be found in Sambrook et al. (Molecular Cloning: A Laboratory Manual, 2nd Edition, Cold Spring Harbor Laboratory press (1989)), and other laboratory textbooks.

Seeding of the Neo-Organ Matrix or Scaffolds

Seeding of cells onto the matrix or scaffold can be performed according to standard methods. For example, the seeding of cells onto polymeric substrates for use in tissue repair has been reported (see, e.g., Atala, A. et al., J. Urol. 148 (2 Pt 2): 658-62 (1992); Atala, A., et al. J. Urol. 150 (2 Pt 2): 608-12 (1993)). Cells grown in culture can be trypsinized to separate the cells, and the separated cells can be seeded on the matrix. Alternatively, cells obtained from cell culture can be lifted from a culture plate as a cell layer, and the cell layer can be directly seeded onto the scaffold without prior separation of the cells.

In a preferred embodiment, in the range of 1 million to 700 50 million cells are suspended in medium and applied to each square centimeter of a surface of a scaffold. Preferably, between 1 million and 50 million cells, and more preferably, between 1 million and 10 million cells are suspended in media and applied to each square centimeter of a surface of a scaffold. The matrix or scaffold is incubated under standard culturing conditions, such as, for example, 37° C., 5% $CO_2$, for a period of time until the cells attached. However, it will be appreciated that the density of cells seeded onto the scaffold can be varied. For example, greater cell densities promote greater tissue regeneration by the seeded cells, while lesser densities may permit relatively greater regeneration of tissue by cells infiltrating the graft from the host. Other seeding techniques may also be used depending on the matrix or scaffold and the cells. For example, the cells may be applied to the matrix or scaffold by vacuum filtration. Selection of cell types, and seeding of cells onto a scaffold, will be routine to one of ordinary skill in the art in light of the teachings herein.

In one embodiment, the scaffold is seeded with one population of cells to form an artificial organ construct. In another embodiment, the matrix or scaffold is seeded on two sides with two different populations of cells. This may be performed by first seeding one side of the matrix or scaffold and then seeding the other side. For example, the scaffold may be placed with one side on top and seeded. Then the matrix or scaffold may be repositioned so that a second side is on top. The second side may then be seeded with a second population of cells. Alternatively, both sides of the matrix or scaffold may be seeded at the same time. For example, two cell chambers may be positioned on both sides (i.e., a sandwich) of the scaffold. The two chambers may be filled with different cell populations to seed both sides of the matrix or scaffold simultaneously. The sandwiched scaffold may be rotated, or flipped frequently to allow equal attachment opportunity for both cell populations. Simultaneous seeding may be preferred when the pores of the matrix or scaffold are sufficiently large for cell passage from one side to the other side. Seeding the scaffold on both sides simultaneously will reduce the likelihood that the cells would migrate to the opposite side.

In another embodiment, two separate scaffolds may be seeded with different cell populations. After seeding, the two matrices may be attached together to form a single matrix or scaffold with two different cell populations on the two sides. Attachment of the scaffolds to each other may be performed using standard procedures such as fibrin glue, liquid co-polymers, sutures and the like.

Surgical Reconstruction

Grafting of scaffolds to an organ or tissue to be augmented can be performed according to the methods described in the Examples or according to art-recognized methods. The matrix or scaffold can be grafted to an organ or tissue of the subject by suturing the graft material to the target organ. Implanting a neo-organ construct for total organ replacement can be performed according to the methods described in the Examples or according to art-recognized surgical methods.

The described techniques may also be used to treat cancer in an organ or tissue. For example, a normal tissue sample may be excised from a patient suffering from cancer. Cell populations from the tissue sample may be cultured for a period of time in vitro and expanded. The cells may be sorted using a florescent activated cell sorter to remove cancerous or precancerous cells. The sorted cells may be used to construct a seeded scaffold. At the same time, the patient may be treated for cancer. Cancer treatment may involve excision of the cancerous part of the organ in addition to chemotherapy or radiation treatment. After the cancer treatment, the seeded scaffold may be used to reconstruct the tissue or organ.

While a method for bladder reconstruction is disclosed in the Examples, other methods for attaching a graft to an organ or tissue of the subject (e.g., by use of surgical staples) may also be employed. Such surgical procedures can be performed by one of ordinary skill in the art according to known procedures.

The present invention will be further understood by reference to the following non-limiting examples.

Example 1

Creation of Bladder-Shaped Polymeric Matrices or Scaffolds

The neo-organ constructs described herein are presented using neo-bladder constructs as an example. While reference is made here to neo-bladder constructs, it will be understood that the methods and materials described herein are useful for creating a variety of neo-organs and neo-vessel augmentation constructs, including, for example, neo-kidney augmentation constructs.

Manufacture of Neo-Bladder Matrix or Scaffold.

The neo-bladder matrices or scaffolds for tissue reconstruction, repair, augmentation, or replacement are constructed using polyglycolic acid (PGA) non-woven felt (BMS 2.5 mm thick, 58 mg/cc or 99 mg/ml). The PGA non-woven felt has an average fiber diameter of about 15 μm, an interfiber distance between about 0 to about 200 μm, and dimensions of about 10 cm by about 10 cm. The starting material for constructing the non-woven felt is PGA or PLGA 10:90 or 15:85, having a molecular weight MW of 100 kDa. The starting material has a 2.5 mm thickness foam, a porosity of approximately 95% and an average pore size of approximately 150 microns.

The PGA non-woven felt is cut using a neo-bladder pattern as a template. The neo-bladder pattern is for example, spherical, quasi-spherical, hemispherical, or quasi-hemispherical in shape, such that bladder repair, or augmentation procedures require one hemispherical or quasi-hemispherical neo-bladder construct, while total bladder reconstruction may require one spherical or quasi-spherical neo-bladder construct, or two hemispherical or quasi-hemispherical neo-bladder constructs joined together to create a spherical or quasi-spherical construct.

To create spherical, quasi-spherical, hemispherical or quasi-hemispherical neo-bladder constructs for repair, augmentation, or replacement, the PGA non-woven felt is cut using a neo-bladder template. The neo-bladder template is a single piece of PGA non-woven felt or multiple pieces that are joined together, e.g., two or more pieces, three or more pieces, or four or more pieces. The template is then assembled, for example, by joining distinct areas of a single template together, or by joining two or more pieces of a multi-piece template together. In one embodiment, a single distinct template is used to form a spherical or quasi-spherical neo-bladder construct. In another embodiment, a single distinct template is used to form two hemispherical or quasi-hemispherical neo-bladder constructs, such that a two-part construct is initially formed from one integral part. In another embodiment, two or more distinct templates are used to create hemispherical or quasi-hemispherical neo-bladder constructs which are adapted to mate to each other, such that each half of the neo-bladder construct is formed from two or more distinct parts. In some embodiments, the two or more distinct templates or parts used to create a hemispherical or quasi-hemispherical parts adapted to mate are symmetrical, while in other embodiments, the two or more distinct templates or parts are asymmetrical.

Augmentation Construct Designs

Single neo-bladder template designs, when assembled, produce a spherical or quasi-spherical construct for use in bladder augmentation. Regardless of the template used, the assembled construct is designed to fit within the geometry of the intended site of implantation, e.g., within a human subject.

An example of an initial, single neo-bladder template used to create a quasi-spherical neo-bladder construct is shown in FIG. 1. The neo-bladder template of FIG. 1, when assembled, creates a unitary construct that is spherical or quasi-spherical. After the pattern shown in FIG. 1 is cut using a die press or manually, the petal portions are mated together. The petal portions can be mated using glue, staples, sutures or other technique known to one of ordinary skill in the art. Preferably, the petal portions are assembled such that at least a portion of each petal overlaps with at least a portion of the adjacent petal, thereby forming a tulip or tulip-like shape. For example, a 4-0 vicryl suture is used to suture each petal together from the inside out, using a simple uninterrupted stitch or "blanket stitch" with a knot every third or fourth stitch. Once two petals are sutured together, loops of suture, e.g., a 1.5 inch loop or a 3 inch loop, are made at the end of every other petal. Preferably, there are six loops per scaffold, one at the end of each petal. Another loop of suture, e.g., a three inch loop, is made at the apex of the scaffold to finish the suturing. These loops form handles for increased ease of manipulation and implantation for the neo-bladder constructs described herein. For example, the surgeon uses these loops as handles to hold onto the neo-bladder construct during implantation.

In other embodiments, the neo-bladder matrix or scaffold is formed using any of a variety of techniques known in the art. The neo-bladder matrix or scaffold is, for example, molded, foamed or electrospun.

Neo-bladder constructs for augmentation may also be formed as a multi-part design, for example, a two-part design or a three-part design. The multi-part constructs use distinct scaffold parts adapted to mate to form a single hemispherical or quasi-hemispherical construct. As used herein, the term hemi-shape denotes one half of any geometrical shape. The hemi-shapes adapted to mate may be symmetrical or asymmetrical. The distinct scaffold parts can be initially formed from a single template as one integral part, or formed from two or more templates as distinct parts adapted to mate to each other.

In the construction of neo-organs, at times it is desirable to access the interior of the construct. For example, access to the interior may be necessary to seed cells on the interior surface of the scaffold, to attach vessels to the interior of the organ, or other manipulation in surgery. After such manipulation, the scaffold parts must be joined to form the neo-bladder construct. The construct design and methods described herein allow for rapid, reproducible, aseptic joining of the scaffold parts.

An example of an initial, asymmetrical two-part design used to create a quasi-spherical neo-bladder construct is shown in FIG. 2. In one embodiment, the two-part neo-bladder construct design includes unseeded flaps for increased ease of manipulation, an outer rim or brim where sutures and adhesives can be used to seal the apical dome and a flanged collar, as shown in FIG. 2. The flaps can be integrally formed with the neo-bladder construct, or they can be made as discrete parts that are stapled in place.

The initial two-part neo-bladder construct design shown in FIG. 2 incorporates tabs that allow the surgeon to maneuver the construct without touching cell seeded areas. This design also includes a flanged collar to help attach the cut edge of the native bladder trigone to the flanged cell seeded neo-bladder scaffold. The flanged collar is constructed from the same scaffold material, but is not seeded with cells. This procedure helps speed up the surgery time for implantation. Briefly, the surgeon will be able to first suture the angled collar to the trigone portion of the remaining bladder, and then be able to remove the neo-bladder construct from the shipping vessel and suture the two flanged edges together to complete the procedure. This two-part system should decrease the amount of time the seeded neo-bladder construct is exposed, and will decrease the stress on the patient. The flanged edges can be sutured together using a continuous simple uninterrupted stitch, rather than multiple stitches to connect the trigone directly to the un-flanged neo-bladder construct. In addition, the surgeon can handle and manipulate the unseeded collar via the tabs during attachment to the trigone portion, and then remove the tabs after the two halves have been joined.

Figure 11A:
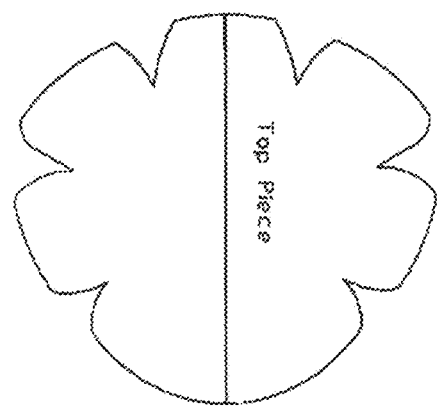
Figure 11B:
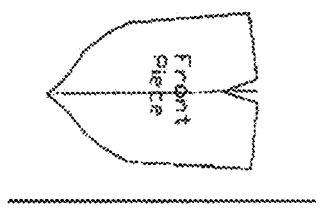
Figure 12A:
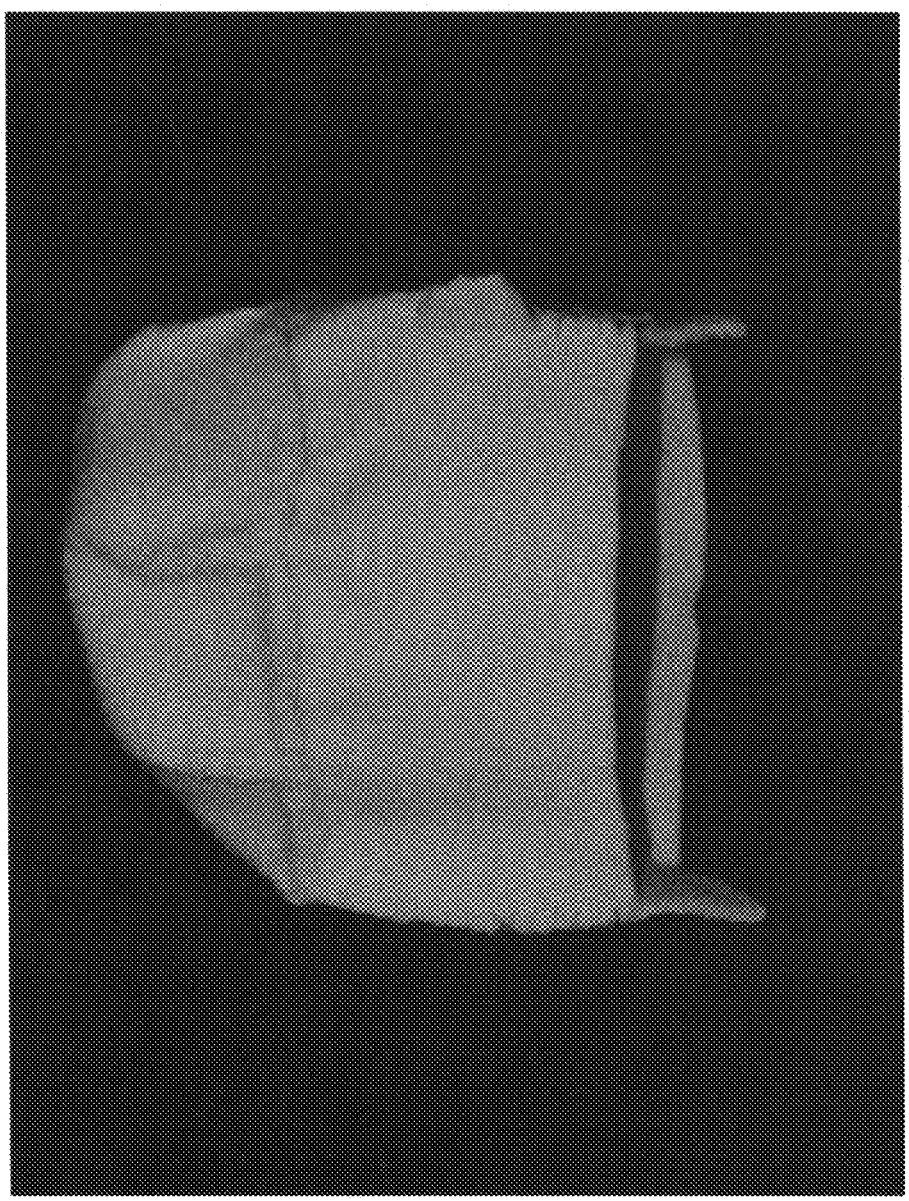
FIGS. 12A-12D depicts the quasi-hemispherical crown shaped neo-organ matrix or scaffold constructed from the three-part template shown in FIGS. 11A-11C.
Figure 12B:
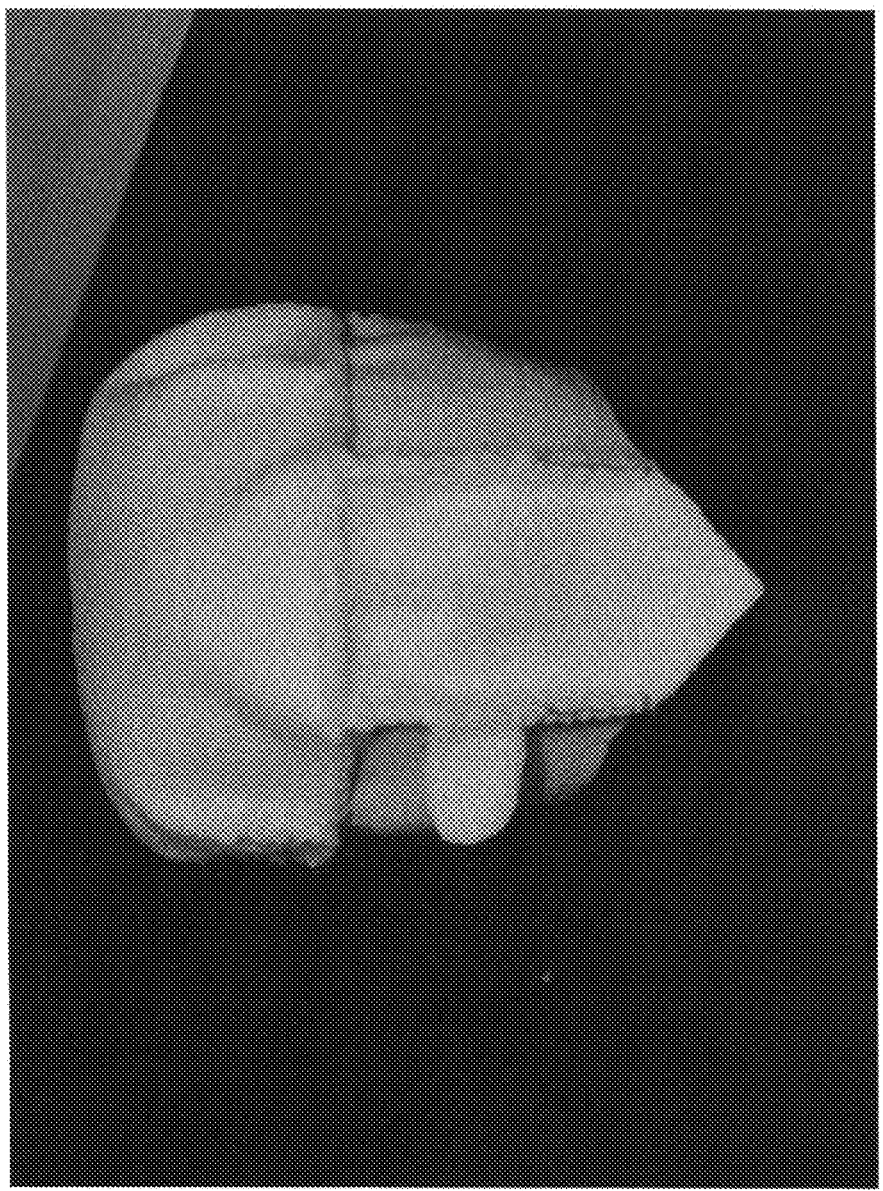
Figure 12C:
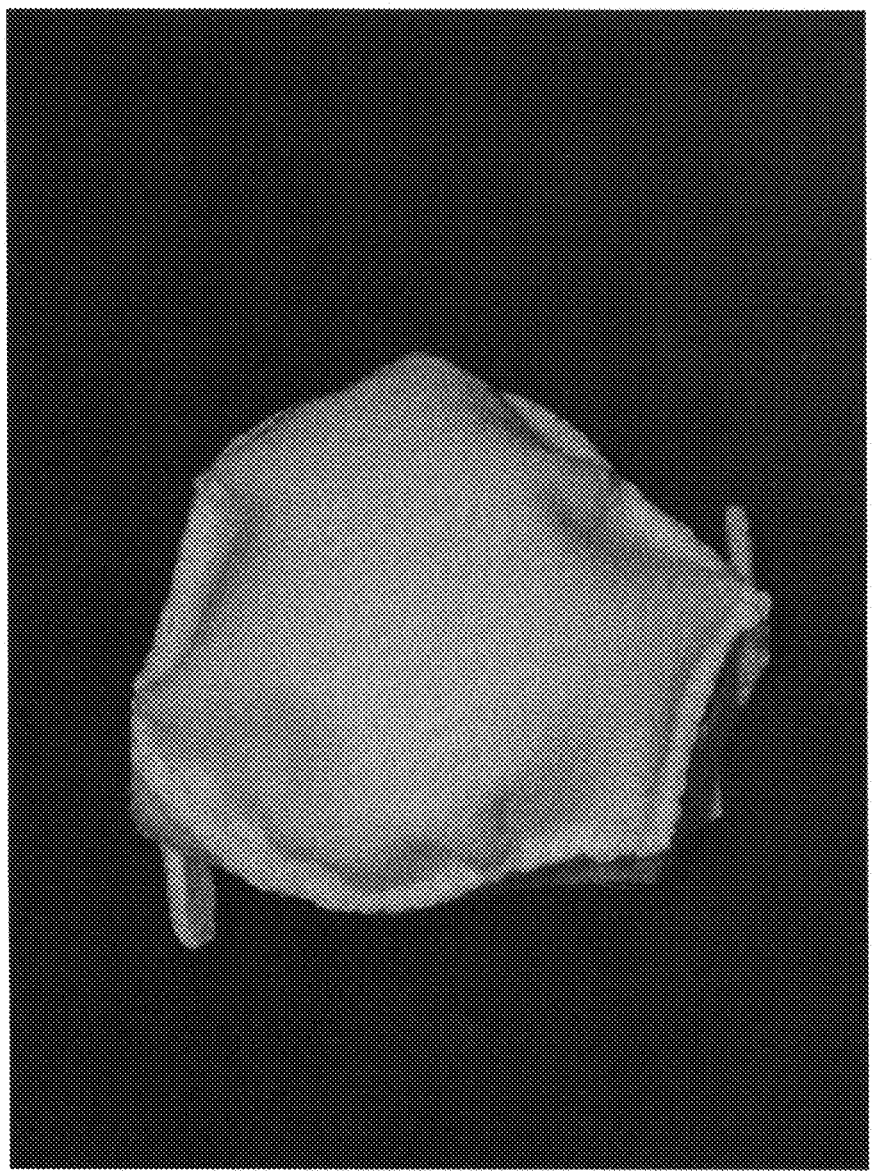
Figure 12D:
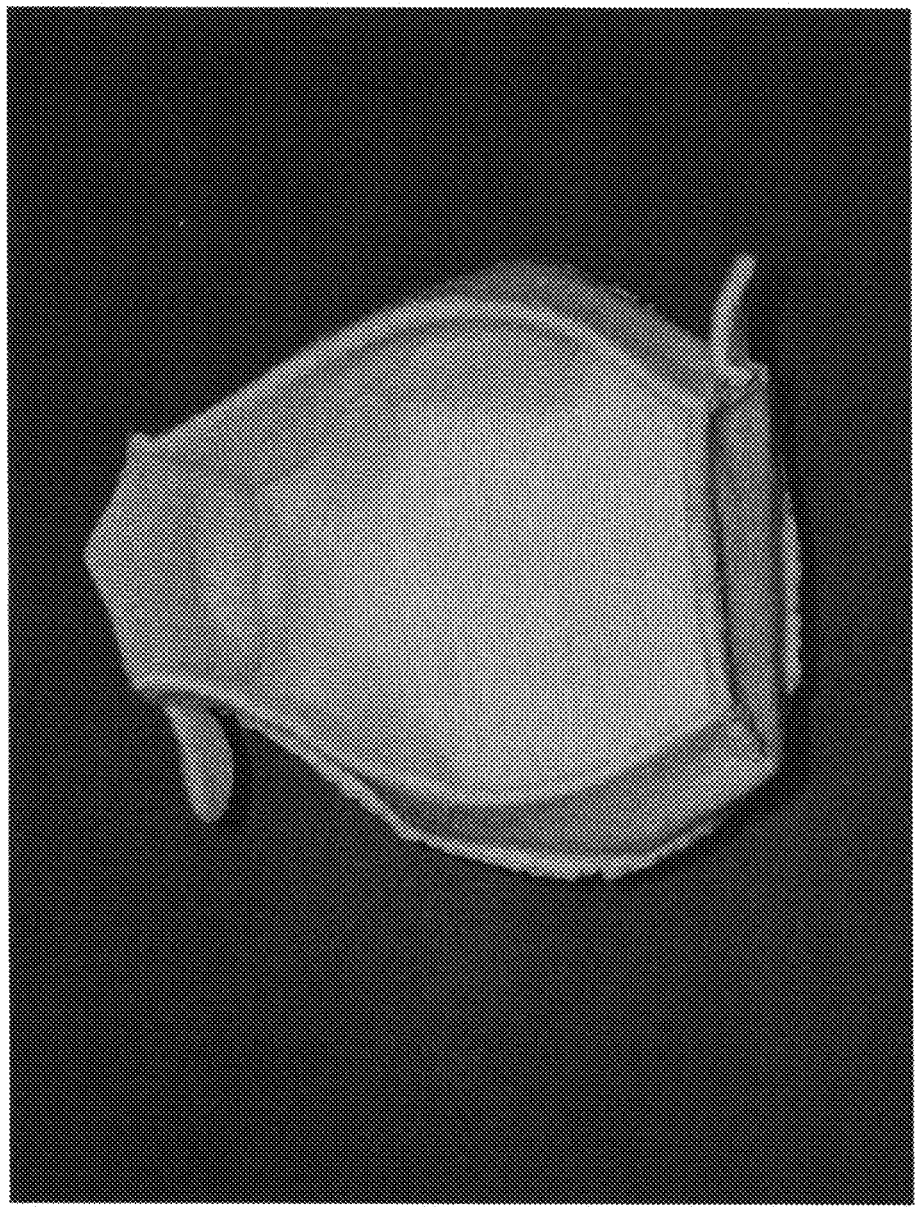

The multi-part neo-bladder construct design was ultimately modified to adapt to the unique geometry of the intended site of implantation. In particular, the multi-part augmentation template was modified such that, when assembled, the construct is crown-shaped or generally crown-shaped to accommodate the geometry of the site of implantation. This can be accomplished using a three-part design to form distinct quasi-hemispherical matrix or scaffold parts. One three-part quasi-hemispherical shape may be used for bladder augmentation or repair. Alternatively, two three-part quasi-hemispherical shapes may be mated to create a quasi-spherical shape for total bladder replacement. An example of three distinct templates used to create a quasi-hemi-spherical neo-bladder construct which can accommodate the geometry of the site of implantation is shown in FIGS. 11A-11C. In one embodiment, the three-part design used to create quasi-hemispherical neo-bladder constructs includes unseeded flaps for increased ease of manipulation, an outer rim or brim where sutures and adhesives can be used to mate the three parts together. The flaps can be integrally formed with the neo-bladder construct, or -they can be made as discrete parts that are stapled or sewn in place.

One advantage of using a three-template design to create distinct quasi-hemispherical scaffold parts is scalability. One of ordinary skill in the art could calculate the appropriate length, width, and height of each of the three templates to scale the patterns up or down, depending on the desired volume of the organ to be augmented or replaced. In one embodiment, the three patterned template shown in FIGS. 11A-11C has an equator length of 8.6 cm, equator width of 8.4 cm, and a height of 7.2 cm is used to create a 250 mL neobladder scaffold. In another embodiment, an equator length of 9.6 cm, equator width of 8.7 cm, and a height of 7.3 cm is used to create a 350 mL neo-bladder scaffold. In yet another embodiment, an equator length of 10.9 cm, equator width of 10.5 cm and a height of 8.3 cm is used to create a 450 mL scaffold.

PGA non-woven felt is cut using the three-part neo-bladder template shown in FIG. 11A-11C. Each of the three parts are then sutured together using three, preferably four, or more than four vertical seams to create a crown shaped construct. An example of the three distinct scaffold parts sutured together using four vertical seams is shown in FIGS. 12A-12D. Preferably, the seams are sutured in such a way as to be cut without unraveling. For example, knotting every stitch in the vertical seams would allow a surgeon to cut and sew without the seams unraveling. Thus, in addition to scalability, this three part-part neo-bladder construct design is advantageous over previous designs in that it also allows flexibility for the surgeon to customize the shape of the neobladder construct to the individual anatomy of the patient at the time of surgery.

Replacement Construct Designs

The two-part constructs for bladder replacement use distinct scaffold parts, preferably at least two hemi-shapes, adapted to mate to form a single spherical or semi-spherical construct. As used herein, the term hemi-shape denotes one half of any geometrical shape. The hemi-shapes adapted to mate may be symmetrical or asymmetrical. The distinct scaffold parts can be initially formed from a single template as one integral part, or formed from two or more templates as distinct parts adapted to mate to each other.

Figure 5:
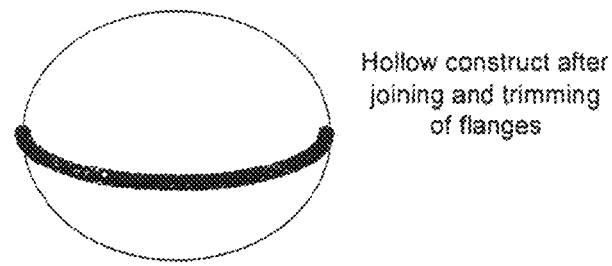
FIG. 5 is an illustration depicting the joined neo-organ matrix or scaffold portions of the scaffold shown in FIG. 4 with trimmed flanges.

An example of an initial, symmetrical two-part design used to create a spherical neo-bladder construct for use in bladder replacement is shown in FIGS. 3-5. In one embodiment, the hemispherical distinct scaffold parts are fabricated with exterior flanges on the seams that need to be joined (FIGS. 3-5). The unseeded flanges are used as handles for manipulation prior to or during surgery. The flanges are used to seal the halves together following manipulation. The lower hemisphere is, for example, placed on a ring which supports the hemisphere by its flange. The upper hemisphere is then placed on top of the lower and its flange is covered with another ring. The rings are squeezed together. Energy, such as heat, RF, and/or ultrasound, is applied to the flanges, joining them together and forming a seal. The energy and pressure soften the molecules at the interface (increasing their mobility, temporarily raising them above the glass transition temperature (Tg)). This allows the molecules from the different flanges to form an interpenetrating network, which results in a rigid seal when the molecules return to their glassy state. The rings may be metal or any sterilizable material.

In addition, the apparatus can be constructed to trim off extra flange material. Preferably, the configuration would leave tabs or handles on the construct for the surgeon to use in manipulating the construct. This type of construct could be set up sterilely in the laminar flow hood to seal the construct immediately following cell seeding, and could be portable and brought into the operating suite for the surgeons to join the construct parts in surgery.

Figure 6:
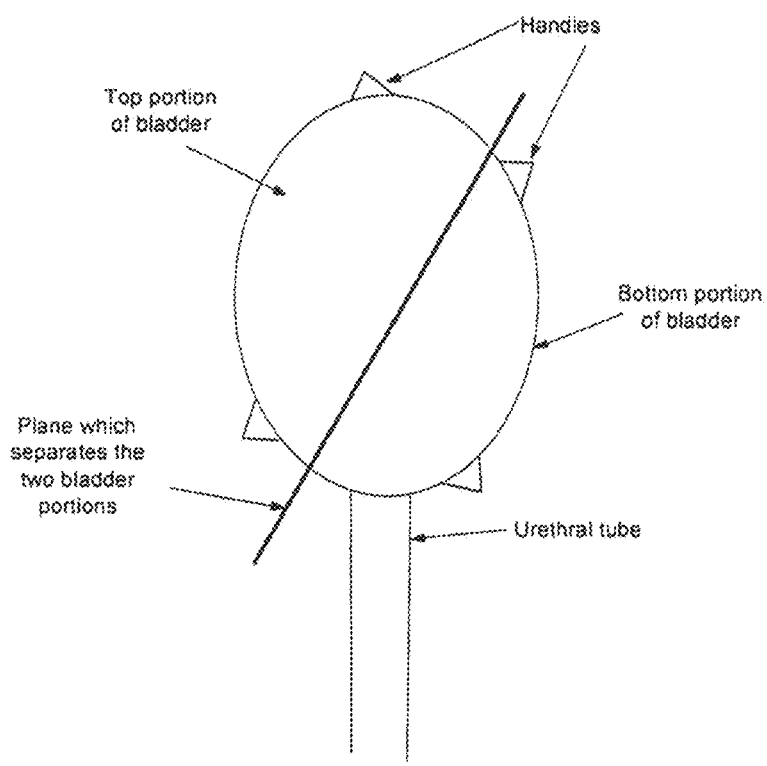
FIG. 6 is an illustration depicting a bisected neo-organ matrix or scaffold design for organ replacement in which the neo-organ matrix or scaffold is bisected along a non-equatorial axis so that the non-equatorial borders of each bisected portion are closer to the tubular structures or vessels to be attached such as the urethral tube.

Another example of an initial symmetrical two-part neo-bladder construct design is shown in FIG. 6. In this alternative design, instead of splitting the neo-bladder into its two parts along an equatorial plane, which is a long distance from the area of urethral attachment, the neo-bladder is bisected next to the structures what allow for urethral attachment. This gives the surgeon easy access to the connections points. This is especially useful when a less spherical—more elongated shape is employed. In this configuration, the halves could be made of at least two separate pieces of scaffold material, adapted to mate. Alternatively, the halves could each be made from one seamless piece of scaffold material, instead of pieces with multiple petals that need to be joined. This system also could be used to provide unneeded flaps or handles that would allow for manipulation prior to and during surgery, and could be removed by the surgeon of left in place (see FIG. 6).

Ultimately, the replacement bladder construct design was modified. In particular, a two-part neo-bladder construct was designed to contain a flanged longitudinal, elliptical opening on one side of construct, and a circular or quasi circular opening the side opposite the longitudinal, elliptical opening, each to allow access to the interior of the construct. The circular and longitudinal, elliptical openings provide access to the interior of the construct, and provide attachment points of urogenital tubes such as the ureters and urethra that optimize the regeneration and proper functioning of the construct-tube junctions.

The template design for a two-part neo-bladder construct with a circular or quasi-circular opening opposite an elliptical, longitudinal opening comprises a base with petals radially extending from the base. The two distinct scaffold parts could be made from one continuous piece of scaffold material which is then cut to form two-distinct parts. In this configuration, the template comprises a base and at least 4 petals, preferably 5 petals, more preferably 6 petals, or more than six petals, radially extending from the base. Once cut, additional scaffold material is optionally added to the base of each half to create unseeded flaps, tabs, or handles that would allow for manipulation prior to and during surgery, and could be removed by the surgeon or left in place. For example, the neo-bladder template is designed such that at least one pair of opposing petals is shorter in length than the other petals. In this design, the construct that is formed when the template is assembled contains an opening at one end of the construct.

Alternatively, the two distinct scaffold parts could be made from multiple pieces of scaffold material. In a preferred embodiment, the two halves are made from 2 separate pieces of scaffold material adapted to mate. In this configuration, the template for each half comprises a base, and at least 2 petals radially extending from the base. Flaps, tabs or handles which are cut from the same scaffold material, may be integrated into the base design to allow for ease of manipulation prior to and during surgery, thereby eliminating the need to attach additional materials to the base to create flaps, tabs, or handles, as shown in FIG. 7.

One of ordinary skill in the art would be able to determine the appropriate circumference or diameter of the base, the appropriate shape, width, and length of each petal, and the appropriate number of petals depending on the shape and size of the organ to be repaired, replaced, or augmented. The size, shape and number of the petals can be scaled up or down to accommodate the geometric site of implantation once the scaffold parts are sutured together or otherwise mated and to control the length of the elliptical, longitudinal, flanged opening and the area of the opening on the side opposite the longitudinal opening. In a preferred embodiment, each half of the template comprises three petals, wherein the first and third petal on each half template are longer than the second petal such that the formation of a circular or semi-circular opening is created where the tips of the petals come together when mated.

Figure 7:
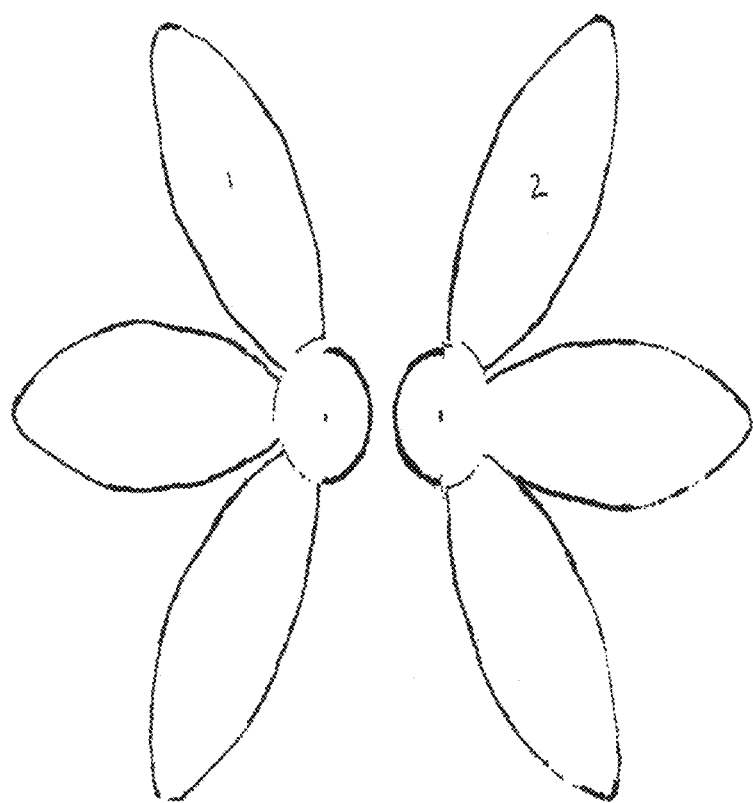
FIG. 7 depicts a two-part neo-organ matrix or scaffold template designed to create, when the two parts are mated, a hollow, quasi-spherical matrix or scaffold with a flanged, longitudinal, elliptical opening on one side, and a circular opening in the surface opposite the longitudinal opening, both openings to allow access to the interior of the matrix or scaffold and to allow for the attachment of tubular vessels to the matrix.

For example, to construct a two-part neo-bladder construct with a circular opening and a longitudinal opening opposite the circular opening, scaffold or matrix material such as PGA non-woven felt is die pressed or manually cut using a neo-bladder template, such as the template shown in FIG. 7. Scaffold or matrix material, such as PGA non-woven felt, is die-pressed or manually cut to create two distinct scaffold parts without a need for additional cutting.

Figure 8:
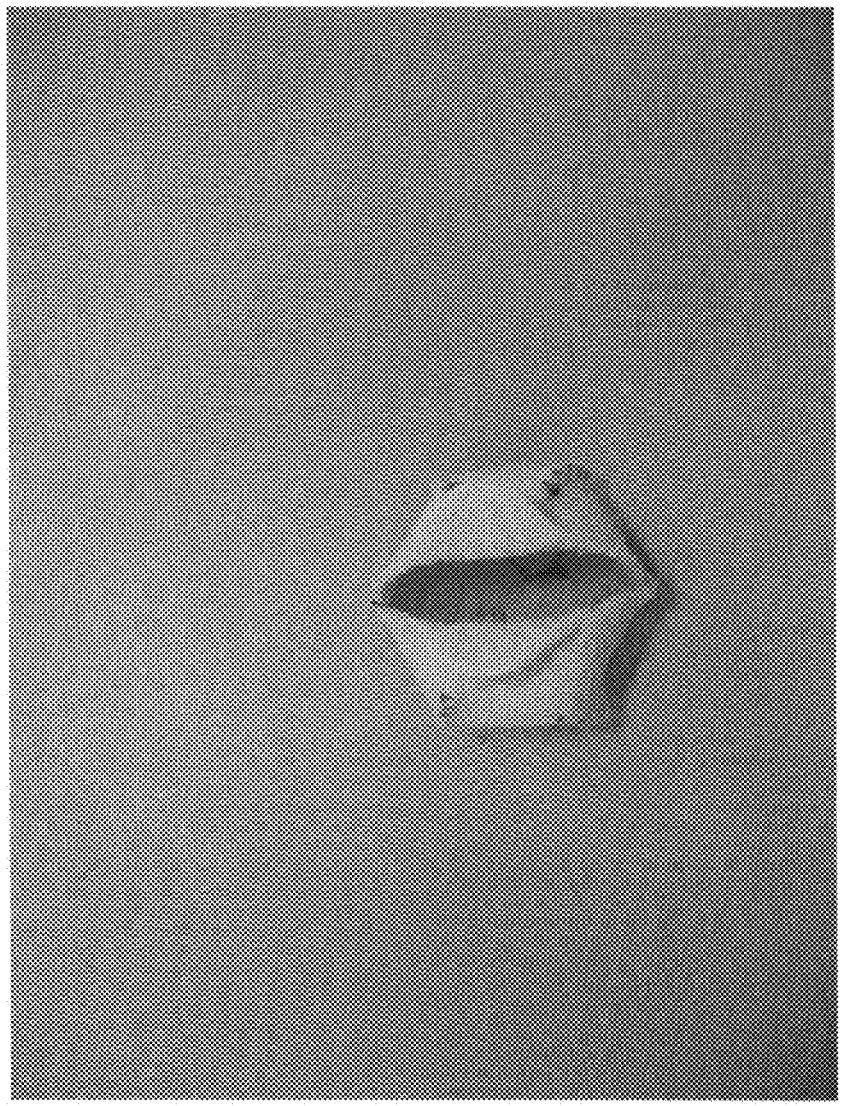
FIG. 8 depicts the top-view of the neo-organ matrix or scaffold constructed from the two-part hollow scaffold template depicted in FIG. 7, showing a longitudinal, elliptical opening at the dome of the scaffold with tabs or flanges on the lips of the opening.
Figure 9:
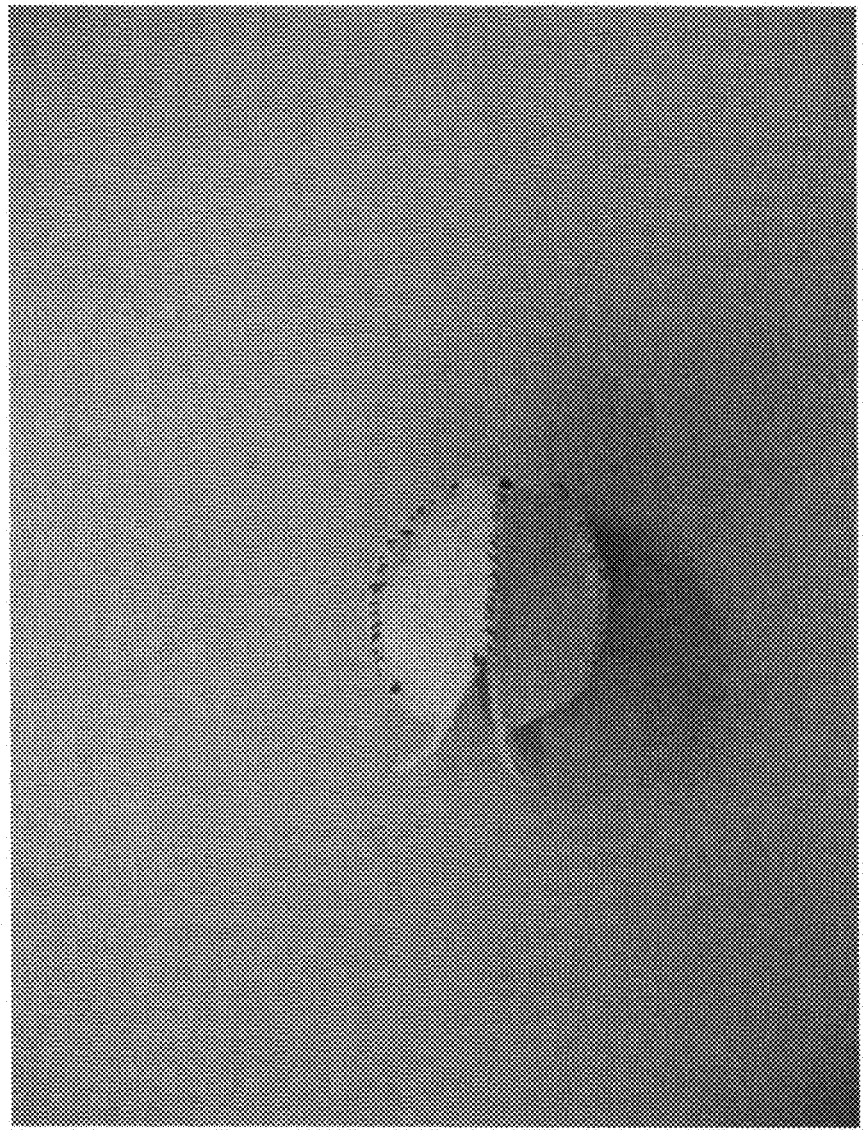
FIG. 9 depicts a side view of the hollow neo-organ matrix or scaffold constructed from the two-part template depicted in FIG. 7.
Figure 10:
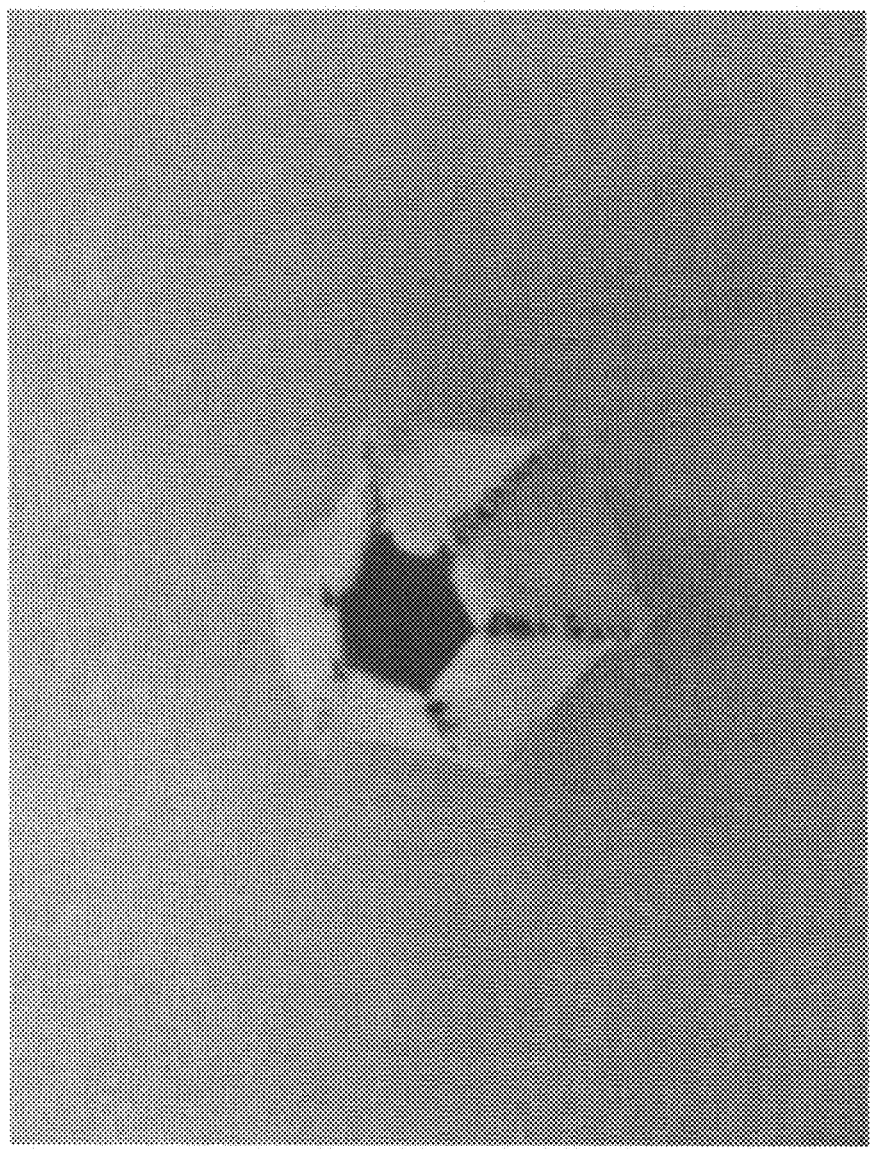
FIG. 10 depicts a bottom view of the hollow neo-organ matrix or scaffold constructed from the two-part scaffold template depicted in FIG. 7, showing the circular opening opposite the longitudinal, elliptical opening depicted in FIG. 8.

Once the scaffold template is cut, the scaffold is constructed by mating the petal portions together. The petal portions may be mated using glue, staples, sutures, or other technique known to one of ordinary skill in the art. For example, a 4-0 vicryl suture, and a simple uninterrupted stitch or "blanket stitch" with a knot every third or fourth stitch, can be used to suture each petal together from the inside out. Once the petals are sutured together, a quasi-spherical shape having 6 vertical seams, with a flanged longitudinal opening on one end (FIG. 8) and a circular or quasi circular opening opposite the longitudinal opening (FIG. 10) is achieved. Depending on the template design used, the longitudinal opening may contain flaps, tabs, or handles on the lip of the opening. For example, in the template design shown in FIG. 7, the two semi-circular bases that face each other in FIG. 7 become the flanged elliptical, longitudinal opening (shown in FIG. 8 and FIG. 9), and tips of the mated petals form the circular opening (shown in FIG. 10) when the two halves of the scaffold parts are mated. The scaffold is then coated with PLGA, seeded with cells and cultured, packaged and shipped to the surgeon.

This two-part neo-bladder design allows a surgeon to attach the scaffold to the urethra using the urethral opening, and access the interior of the construct to attach the ureters using the longitudinal opening on the dome of the scaffold, and using the flaps, tabs, or handles on the lips of the longitudinal opening (if incorporated). The construct is then sutured closed, any flaps, tabs, or handles removed, resulting in a neo-bladder that is essentially equivalent to the one piece unit described in FIG. 1, with no latitudinal seams to interfere with cell migration from the urethra.

This two-part neo-bladder construct containing a first opening at one end and a longitudinal opening opposite the first opening is advantageous over previous designs in that it also allows each of the ureters to be attached at each distal end of the longitudinal opening. Previous neo-bladder scaffold designs which require attachment of the ureters through openings at the bottom (recapitulating a trigone-like structure), or through openings nearer the top of the construct risk the two ureters merging with the urethra or merging into one another as the bladder regenerates. This risk is avoided when the ureters are attached at each distal end of the longitudinal opening, as far from each other as possible within the geometry of the neo-bladder construct. Additionally, the longitudinal opening enables the ureters to be attached at an angle, recapitulating ureteral valves as the bladder regenerates.

In some embodiments, the two-part neo-bladder replacement constructs describe herein are designed such that one or more of the distinct scaffold parts contain holes, receptacles or ports adapted to receive one or more flanged tube inserts, with washers or without washers, to facilitate attachment of urogenital tubes to the neo-bladder construct, as described in Example 9. In some embodiments, the two-part neo-organ constructs described herein contain holes, ports, or receptacles adapted to receive one or more self-stabilizing inserts, as described below in Example 9.

The two-part neo-bladder constructs for replacement, augmentation and/or repair provide a variety of advantages. For example, fabricating the halves of the two-part neo-organ constructs described herein from seamless pieces reduces fabrication steps and complexity. Placing the bisecting plane and/or creating a longitudinal opening near the area of greatest surgical manipulation allows the surgeon easier access to features which need to be sutured or otherwise manipulated during surgery. Unseeded flaps or handles that are integral to the construct provide the surgeon with another method of easily manipulating the construct. In embodiments where the halves are pre-joined, the surgeon is sent an intact sphere, thereby eliminating the need for suturing the halves together during surgery, which, in turn, reduces surgery time and gives a more consistent product. For instance, pre-joining the halves allows for rapid joining of the parts in surgery, after suturing vessels to the interior of the construct. In other embodiments where the halves are joined after coating and forming, but prior to seeding, the interior can be examined and manipulated during the coating process. The presence of the flange material creates handles that could be trimmed off during the sealing process. Alternatively, the flange material can be trimmed to leave small handles for additional manipulation.

Neo-Bladder Matrix or Scaffold Prewetting, Coating, and Sterilization.

A 5% solution of Poly-DL-lactide-glycolide (5% PLGA) is prepared by weighing out 5 g of Poly-DL-lactide-glycolide 50:50 beads and placing the beads into 500 ml glass bottle. 100 ml dichloromethane is added to the bottle, and the solution is stirred at room temperature for at least one hour to allow the beads to dissolve. After 5% PLGA is dissolved, a pre-wetting solution is prepared by adding 100 ml dichloromethane to a 250 ml beaker. Using either hemostats or forceps to manipulate the scaffold and using the scaffold suture handles, the shaped scaffold undergoes pre-wetting by submerging the scaffold in a 250 ml beaker containing 100 ml dichloromethane. Once the scaffold is completely wet, it is removed from the beaker, and the excess liquid is allowed to drain. The scaffold is coated by submerging the scaffold in the 250 ml beaker containing 5% PLGA for two seconds. The coated scaffold is removed from the solution and shaped into the form of a parachute by holding the suture handles with either a hemostat or forceps, while drying the scaffold using a stream of cool air, e.g., by placing the scaffold under a blow drier set on "cool." Once dry, the scaffold is placed in the fume hood for an additional 2 hours to allow further solvent evaporation. The process described above is repeated for a second coating. The coated scaffold is then placed under vacuum for 2 days. At the end of this time, the coated scaffold is placed into foil bag, sealed, and sterilized at 30° C. using ethylene oxide. Prior to sterilizing the coated scaffold, a reinforcing natural or synthetic material can be added to the coated polymer construct through physical attachment using suture material or other physical and/or chemical means to attach the reinforcing material to the bladder polymer.

Pre-Wetting of Neo-Bladder Matrix or Scaffold Prior to Cell Harvesting.

Prior to cell harvesting, e.g., one day prior to harvesting cells, a sterilized scaffold undergoes a pre-wetting procedure. For example, in neo-bladder constructs seeded with smooth muscles and urothelial cells, the coated scaffold undergoes pre-wetting one day prior to harvesting the smooth muscle cells (SMC). The scaffold is pre-wet by adding 500 ml of SMC growth medium (described below) to a pre-wetting container, such as a sterilized 1 liter Nalgene polypropylene jar with a screw cap lid with a Teflon seal. The pre-wetting container is placed in a vacuum chamber, and vacuum is applied to the chamber. When air bubbles are no longer observed and the scaffold is completely wet, remove the pre-wetting container from the vacuum chamber. The pre-wetting container is closed and allowed to sit overnight.

For watertight constructs, the lining of the scaffolds is fragile and cannot withstand much mechanical force. Therefore, prewetting with ethanol is the preferred method. (See Ishaug et al., J Biomed Mater Res.; 36 (1):17-28 (1997)). Use of ethanol as a wetting agent involves minimal mechanical stress put on the construct in contrast to previously used methodologies that involve pipetting medium through the scaffold to ensure adequate wetting.

The procedure for wetting with ethanol is as follows. In the biosafety cabinet (BSC), 100% ethanol is placed in a sterile container in an amount sufficient to cover the scaffold. The same amount of 75% ethanol, 25% PBS; 50% ethanol, 50% PBS, 25% ethanol, 75% PBS, and 100% PBS is placed in sequential containers. In the BSC, the sterile scaffold is removed from its packaging and placed into the first container with forceps. Alternatively, the scaffold, which is attached to the insert, is removed from sterilization container and placed into the ethanol. After 20 minutes, the scaffold is moved to the 75% ethanol container. Every twenty minutes, the scaffold is moved to the next higher PBS concentration. After 20 minutes in 100% PBS, the scaffold is placed in DMEM medium supplanted with gentamicin (50 ug/ml final concentration) overnight. Vacuum can be applied at any stage of the process to facilitate wetting, or the solutions can be gently agitating in the containers, either with stir bar or rocker.

Example 2

Cell Harvest and Culture

Biopsy procurement. In contrast to previous studies in which a 1×1 cm biopsy was taken from the side of the bladder using a scalpel to dissociate the tissue, the tissue samples used to create the neo-bladder constructs described in this Example were obtained by taking a 1×1 cm biopsy from the bladder apex, using a staple method. Previous biopsy procedures, such as the methods described in U.S. Pat. No. 6,576,019 by Atala et al., removed tissue from the vesical dome in general. In contrast, the biopsy procedures used herein remove tissue from a specific portion of the vesical dome, the bladder apex. Removing tissue from the bladder apex has been shown to provide a greater yield of useful cells. Useful cells refers to viable cells that are capable of expansion and seeding on the neo-bladder scaffolds described herein The staple method used herein involves making a loop in the apex of the bladder, stapling the base of the loop, and excising the loop. The staple biopsy provides several advantages over a scalpel biopsy, including, for example, an increase in the amount of tissue safely removed and a concomitant decrease in deleterious effects for the animal. Cells isolated from biopsy material procured in this manner demonstrated superior in vitro attachment and proliferation compared to cells isolated from biopsies obtained from the bladder side using a scalpel. Unlike previous studies where the biopsy material is transported in a standard culture medium such as DMEM supplemented with the standard antibiotic penicillin/streptomycin, the biopsy samples used to create the neo-bladder constructs described herein are transported in a transport medium in which DMEM medium has been supplemented with the broader-spectrum antibiotic gentamicin (50 ug/ml final concentration) to decrease the incidence of receiving contaminated biopsy specimens. This broader-spectrum antibiotic gentamicin has been approved for use in a variety of subjects, including humans. All subsequent manipulations on the biopsy sample are performed under aseptic conditions, e.g., within the confines of a biosafety cabinet (BSC). Urothelial and smooth muscle cell populations, dissociated the bladder biopsies, are routinely expanded and passaged separately as described below.

Urothelial Cell Extraction and Plating:

The biopsy is placed into a sterile plastic tissue culture dish containing 3 ml of medium, referred to herein as Urothelial Cell (UC) medium, which contains 500 ml KSFM supplemented with 25 ug/ml bovine pituitary extract (BPE), 0.1-0.2 ng/ml of recombinant epidermal growth factor (rEGF), and 5 ug/ml gentamicin. Using microsurgical forceps and a scalpel, the urothelial surface of the biopsy is scraped repeatedly into the medium. This method results in the liberation of more cells, with increased viability and vitality, compared to previously used methods involving long periods of biopsy incubation with proteolytic enzymes. The urothelial cells (UC) are then collected by pipetting, and the viability and total cell number are determined by microscopic counting using a hemcytometer. Appropriate dilutions are then made and the cells are plated. The cultures are maintained in a humidified 37° C. incubator in 5% CO2.

Urothelial Cell Expansion.

When cells are nearly confluent (i.e., the surface of the culture vessel is 75-90% covered with cells), the dishes are washed with PBS containing 5 0.5 mm EDTA (PBS/EDTA). The cells are incubated in PBS/EDTA for 5-15 min. at room temperature in the BSC. The PBS/EDTA is aspirated from culture dishes. 0.25% Trypsin/EDTA is added to the dishes, which are then incubated for 5-10 minutes at room temperature in the BSC. The PBS/EDTA incubation step reduces the amount of time the cells need to incubate in the harsher 0.25% Trypsin/EDTA solution. This results in less damage to the cell membranes and is reflected in a greater population of viable cells capable of attaching to the culture dishes in subsequent passages. The cells are then collected from plate and combined into sterile 50 ml conical tube(s) or 225 ml conical bottle(s). Trypsin is neutralized by adding FBS to a final concentration of 0.5%: The cell suspension is centrifuged at room temperature for 5 minutes at 300 g. The aqueous layer is aspirated from cell pellet. The pellet is then resuspended for cell counting in UC growth medium. Viable and non-viable cells are counted. The cells are plated so as to achieve a plating density of between 4,000-10,000 viable cells/cm$^2$. The culture dishes, e.g., P150 culture dishes, are placed into a humidified 37° C. incubator in 5% CO2. This process is repeated until final harvest of cells, which occurs at passages 4-6 (P4-P6).

Smooth Muscle Cell Extraction and Plating.

After extracting UC, the biopsy sample is placed in a P100 dish, and the mucosal layer is trimmed into approximately 1 mm diameter pieces using microsurgical scissors, forceps and/or scalpel. The minced tissue pieces are distributed evenly on the bottom of a labeled sterile tissue culture dish. 10 ml (for P100s) or 25 ml (for P150s) SMC growth medium (DMEM supplemented with 10% FBS and 5 ug/ml gentamicin) is added to gently moisten and submerge tissue fragments without dislodging them from the tissue culture dish, and the dish is placed into humidified 37° C. incubator in 5% CO2.

Smooth Muscle Cell Expansion.

When smooth muscle cells (SMC) are nearly confluent (i.e., the surface of the culture vessel is 75-90% covered with cells), the dishes are washed with phosphate buffered saline (PBS). Cells are incubated in PBS for 2-5 minutes at room temperature in the BSC. PBS is aspirated from culture dishes. 0.05% Trypsin/EDTA is added to dishes, which are incubated for 5-10 minutes at room temperature in the BSC. Cells are collected from the plate and combined into sterile 50 ml conical tube(s) or 225 ml conical bottle(s). Trypsin is neutralized by adding a volume of SMC growth medium that equals approximately 10-20% of the recovered cell suspension volume. The cell suspension is centrifuged at room temperature for 5 minutes at 300 g. The aqueous layer is aspirated from cell pellet, and the pellet is resuspended for cell counting in SMC growth medium. Viable and non-viable cells are counted. Cells are plated so as to achieve a plating density of 4,000-10,000 viable cells/cm$^2$. The flasks or cell factories are placed into a humidified 37° C. incubator in 5% CO2. This process is repeated until final harvest of cells, at passages 4-6 (P4-P6).

Example 3

Cell Seeding on a Polymeric Matrix or Scaffold

Neo-bladder matrix or scaffold seeding with SMC.

Figure 13:
FIGS. 13 and 14 are illustrations depicting the initial seeding vessel and bioreactor for use in seeding and growing neo-organ matrices or scaffolds. Note that the bioreactor must 5 be opened completely to seed and change medium.
Figure 14:
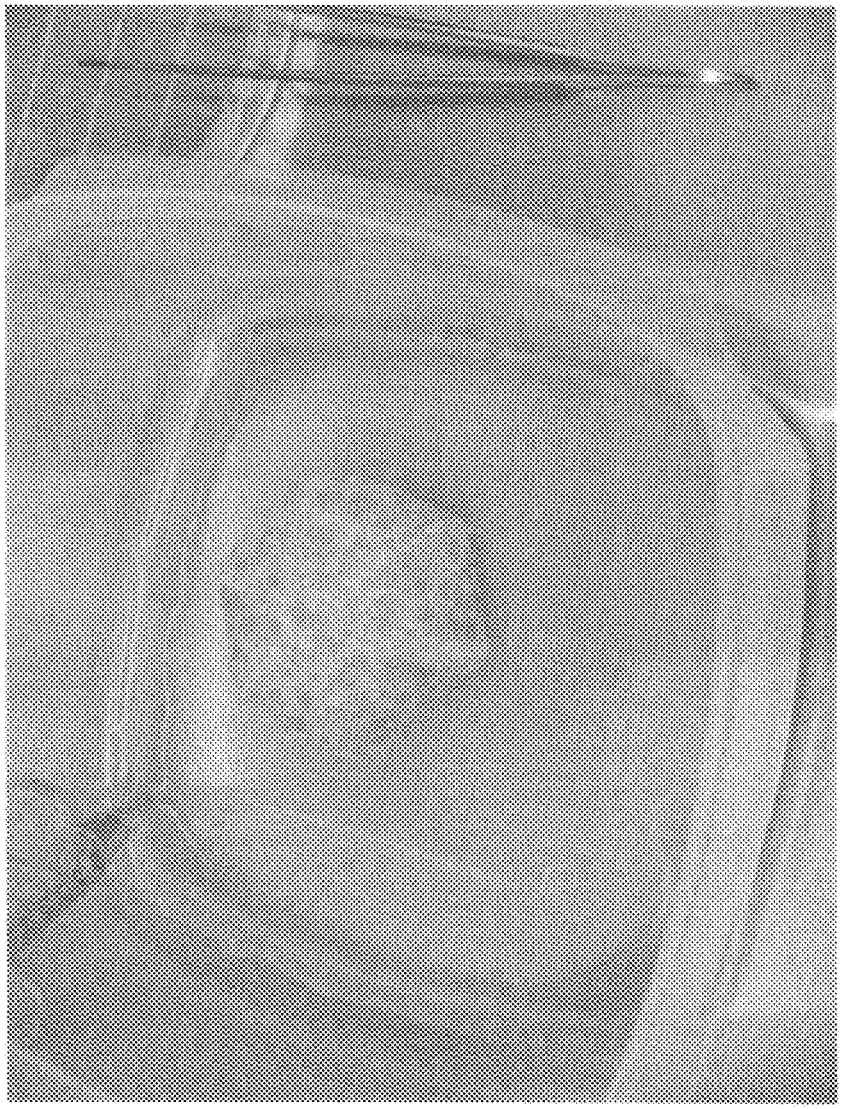

After the smooth muscle cells (SMC) are harvested and expanded as described above in Example 2, the cell pellet is resuspended in 6 ml of SMC growth medium. The matrix or scaffold is removed from the pre-wetting container using forceps and is placed in an empty sterile cell-seeding container (see FIGS. 13 and 14, originally designed and manufactured by Tengion Inc.). In one embodiment, the cell-seeding container utilizes a Rubbermaid plastic three quart container as a seeding vessel and bioreactor for the culture period prior to shipping. The container is wider than it is tall which is useful when seeding the matrix or scaffold with cells. The lid of the container can be removed when the seeding of the neo-bladder takes place. The lid can then be closed and sealed utilizing a PALL acro-0.2 um PTFE filter disc for gas exchange. This seeding container can hold up to two liters of medium which is changed daily for 6 days prior to shipping. The volume of culture medium is enough to maintain cells during the culture period. The sealed container can be moved between the BSC and incubator in order to change medium and seed bladder cells. The design of the seeding container/bioreactor facilitates manipulation of the scaffold in any orientation to better distribute the bladder cells evenly.

In one embodiment of the methods of the present invention, the neo-bladder matrix or scaffold formed by the template depicted in FIG. 1 is seeded as follows. Using a 50 ml pipette, SMC growth medium is added to any scaffold surface that appears dry. All medium is then removed from the cell-seeding container. Using a 10 ml pipette, approximately 6-7 ml of medium is aspirated from the matrix or scaffold, as possible. This aspiration step provides a defined, minimum volume of cell suspension which may be taken up by the scaffold. Alternatively, medium is absorbed from the scaffold by blotting with sterile gauze. Using a P1000 pipettor, one sixth of the cell suspension is taken and seeded on one petal of the scaffold on the outside surface. The cells are distributed evenly on the petal. To prevent cell loss, care is taken not to allow any fluid to drip out of the matrix or scaffold. The remaining five petals are seeded using the procedure described above. Adding the cell suspension drop-wise on each petal ensures a more consistent and even distribution of cells over the scaffold surface, thereby promoting the regenerative process and function of the neo-bladder construct. The drop-wise addition is an improvement over previous methods whereby the cell suspension was washed over the scaffold surface, or the scaffold was dipped into the cell suspension. Once seeding of the petals has been completed, 10-15 ml of SMC growth medium are added around the outer edges of the cell seeding container to create a humidity chamber without the medium touching the seeded construct. The cell-seeding container is sealed and placed in the incubator. After 2-4 hours, the cell-seeding container is removed and placed in the BSC. The cell-seeding container is carefully opened, and 150 ml of SMC growth medium is added into the cell-seeding container. The cell-seeding container is closed again and placed in the incubator overnight. On Day 2 (i.e., the next day after seeding scaffold), the cell-seeding container is removed and placed in the BSC.

Figure 15:
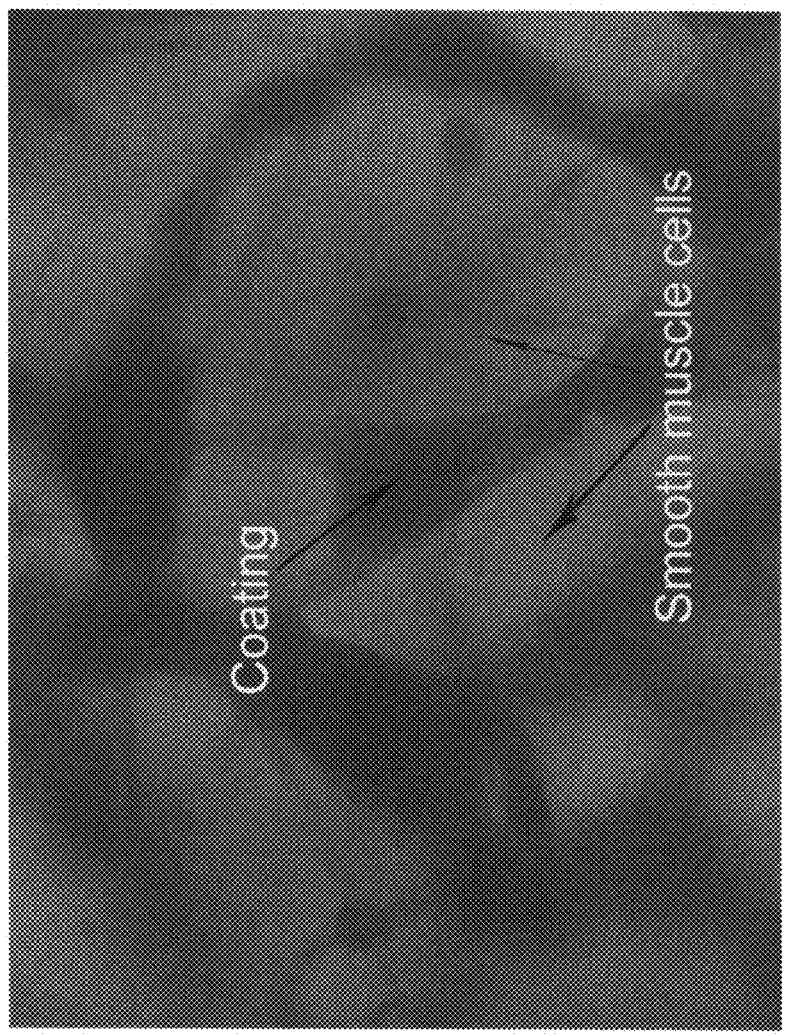
FIG. 15 is an illustration the presence of smooth muscle cells on and in the polymeric matrix of a neobladder scaffold.

The cell-seeding container is carefully opened, and 1.5 L of SMC Growth medium is added to the container (or to the top of container). The cell-seeding container is closed again and placed in the incubator. Bright field microscopy (FIG. 15) confirmed that SMC do indeed take up residence within scaffolds seeded using the procedures described above.

Neo-Bladder Scaffold Seeding with Urothelial Cells.

Figure 16:
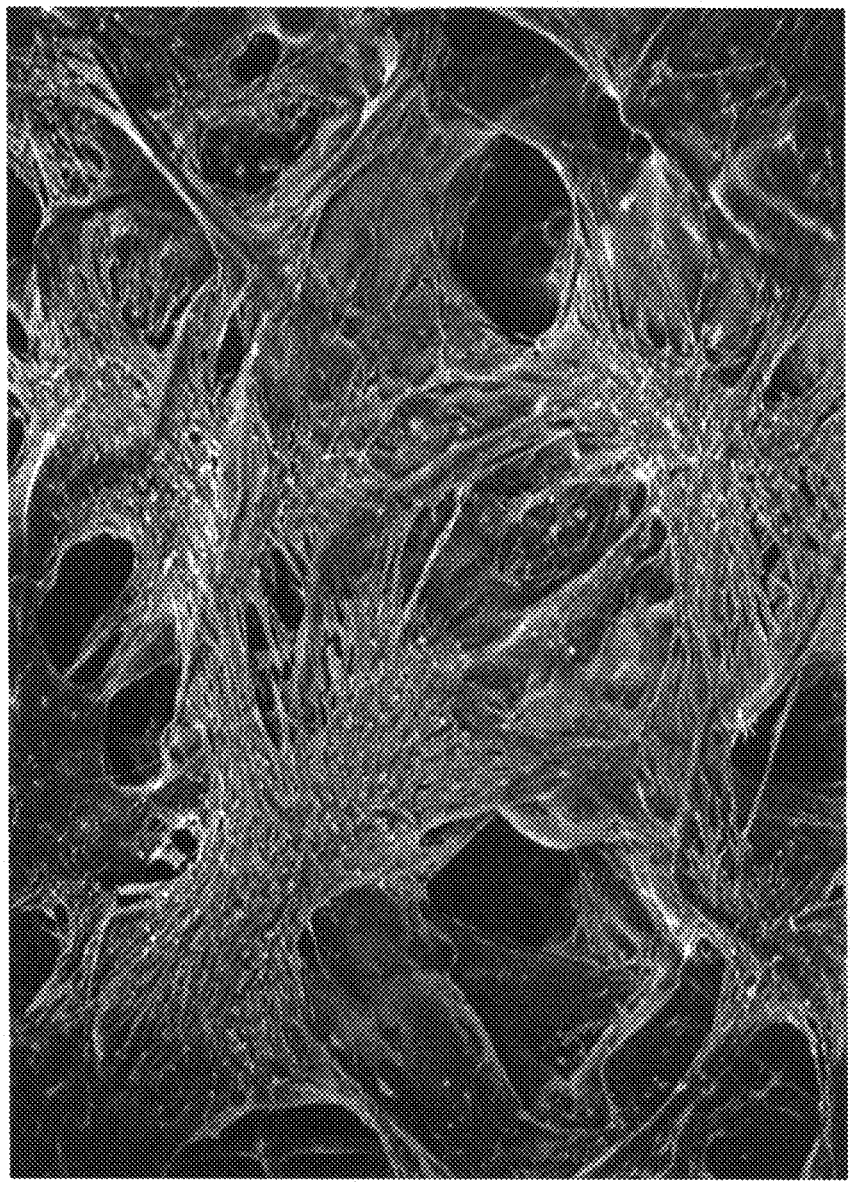
FIG. 16 is an illustration depicting the presence of urothelial cells on and in the polymeric matrix of a neobladder scaffold.

After the urothelial cells (UC) are harvested and expanded as described above in Example 2, the cell pellet is resuspended in 6 ml of Construct Growth Medium 1:1 mixture of DMEM/10% FBS:KSFM). On Day 3 (i.e., the next day after feeding the SMC-seeded scaffold), the cell-seeding container with the SMC-seeded scaffold in SMC growth medium is removed from the incubator. The medium is removed from the cell-seeding container. A 10 ml pipette is used to aspirate 6 ml medium from the scaffold. As mentioned above, this step provides for a defined, minimum volume of cell suspension which may be taken up by a neo-bladder scaffold formed from the template design depicted in FIG. 1. A sterile 5 ml pipette is used to take one sixth of the cell suspension and seed the cell suspension on a pellet of the scaffold on the inside surface. The cells are distributed evenly on the pellet, no fluid is allowed to drip out of the scaffold to prevent cell loss. The remaining five petals are seeded using the procedure described above. The drop-wise addition of the cell suspension on each petal ensures a more consistent and even distribution of cells over the scaffold surface, which is an improvement over previous methods whereby the cell suspension was washed over the scaffold surface, or the scaffold dipped into the cell suspension. Once completed, 10-15 ml of Construct Growth Medium are added to the outer edges of the cell-seeding container to create a humidity chamber without medium touching the construct. The cell-seeding container is sealed and placed in the incubator. After 2 hours, the cell-seeding container is removed and placed in the BSC. The cell-seeding container is carefully opened, and 150 ml of Construct Growth Medium is added into the container. The cell-seeding container is closed and placed in the incubator overnight. On Day 4 (i.e., the next day after UC cell seeding), the cell-seeding container is removed from the incubator and placed in the BSC. Construct Growth Medium is added to fill the cell-seeding container (−1.5 L). The cell-seeding container is closed and placed in the incubator. On Day (the next day), the container is removed from the incubator and placed in the BSC. Medium is aspirated from cell-seeding container, and Construct Growth Medium is added to fill the cell-seeding container (−1.5 L). The cell-seeding container is closed and placed in the incubator. Electron microscopy (FIG. 16), following a 6 day incubation, confirmed that scaffolds seed with UC using the procedures described herein do indeed take up residence within the scaffold.

Example 4

Packaging and Shipping of Cell Seeded Neo-Bladder Constructs

Figure 17:
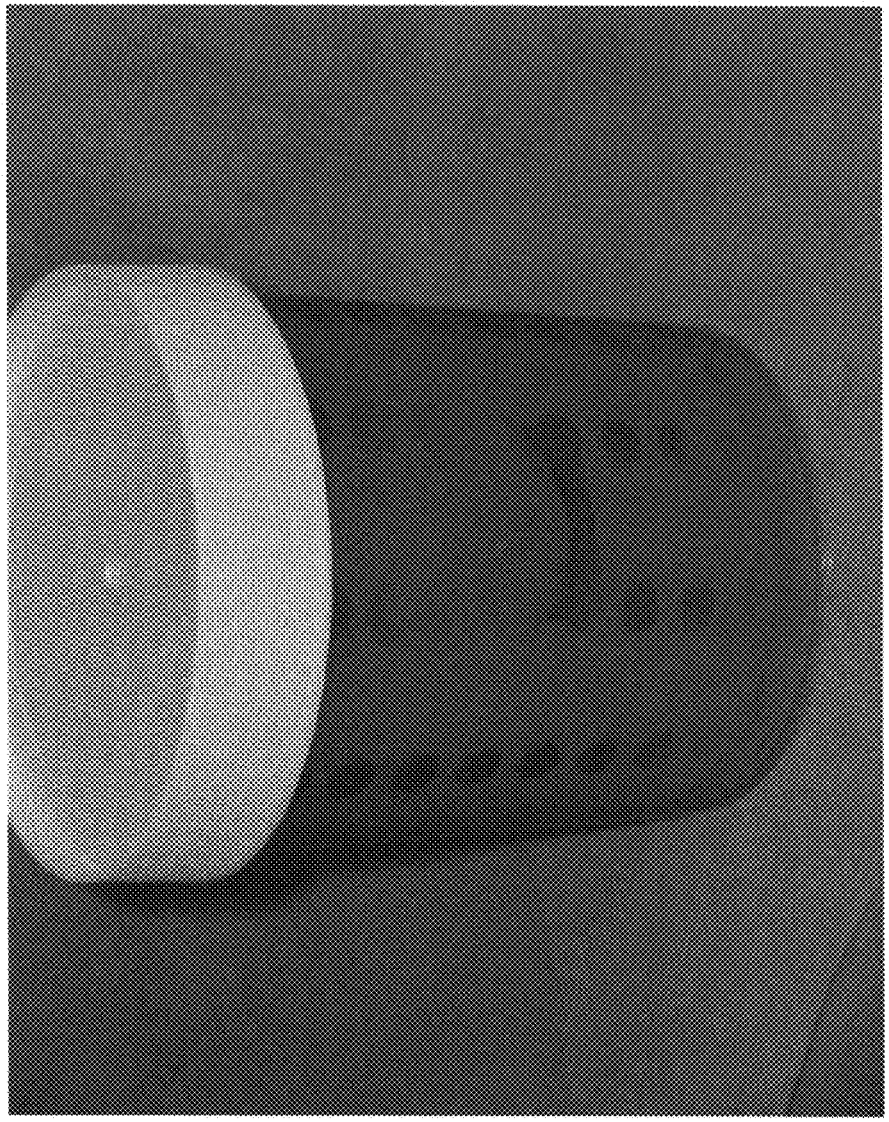
FIGS. 17-20 are illustrations depicting containers for packing and shipping cell-seeded neo-organ scaffolds. Note that the neo-bladder must be removed from the seeding bioreactor and manipulated with hemostats and forceps for attachment to the inner basket of the shipping container.
Figure 18:
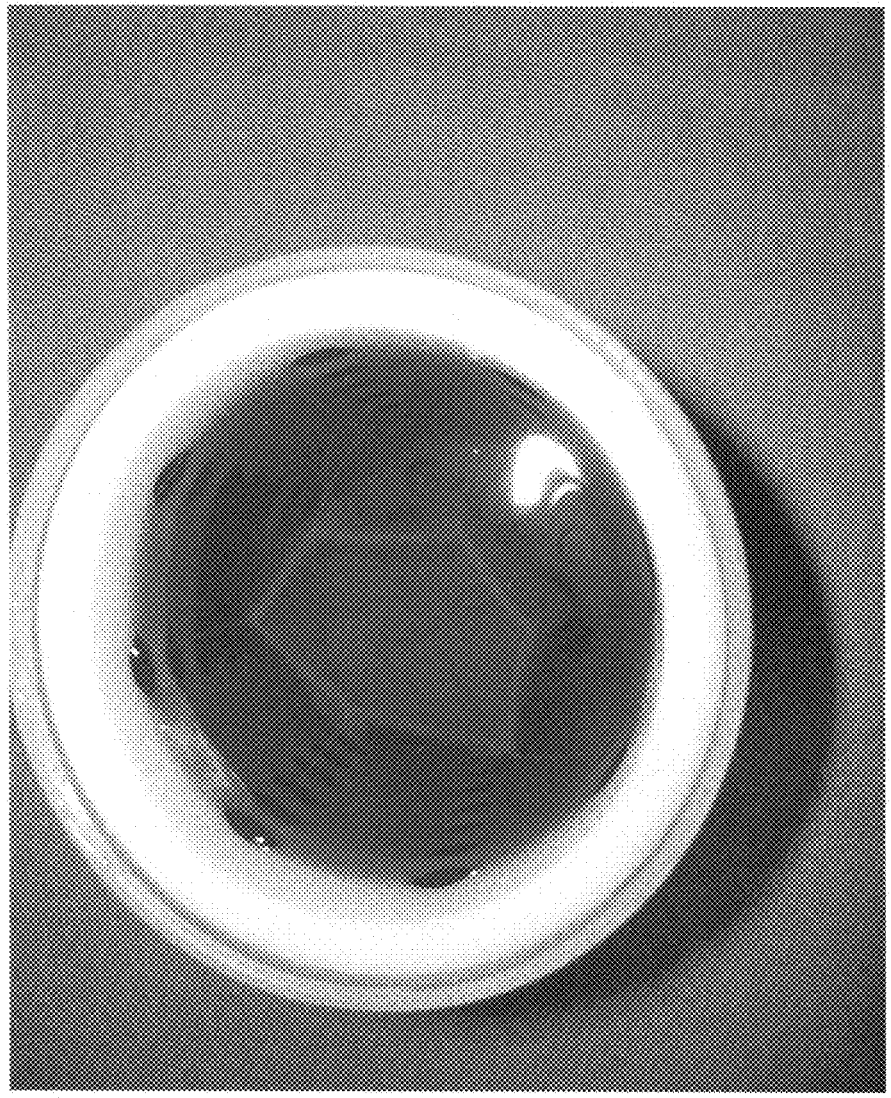
Figure 19:
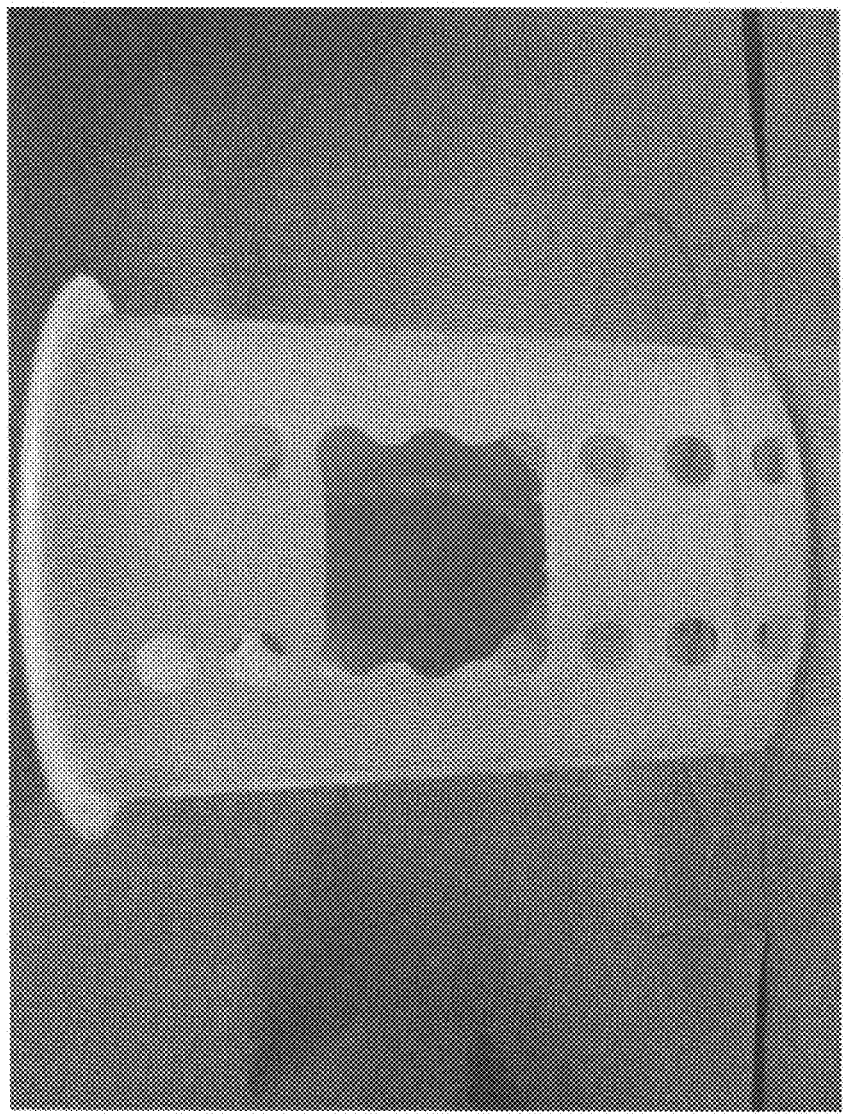
Figure 20:
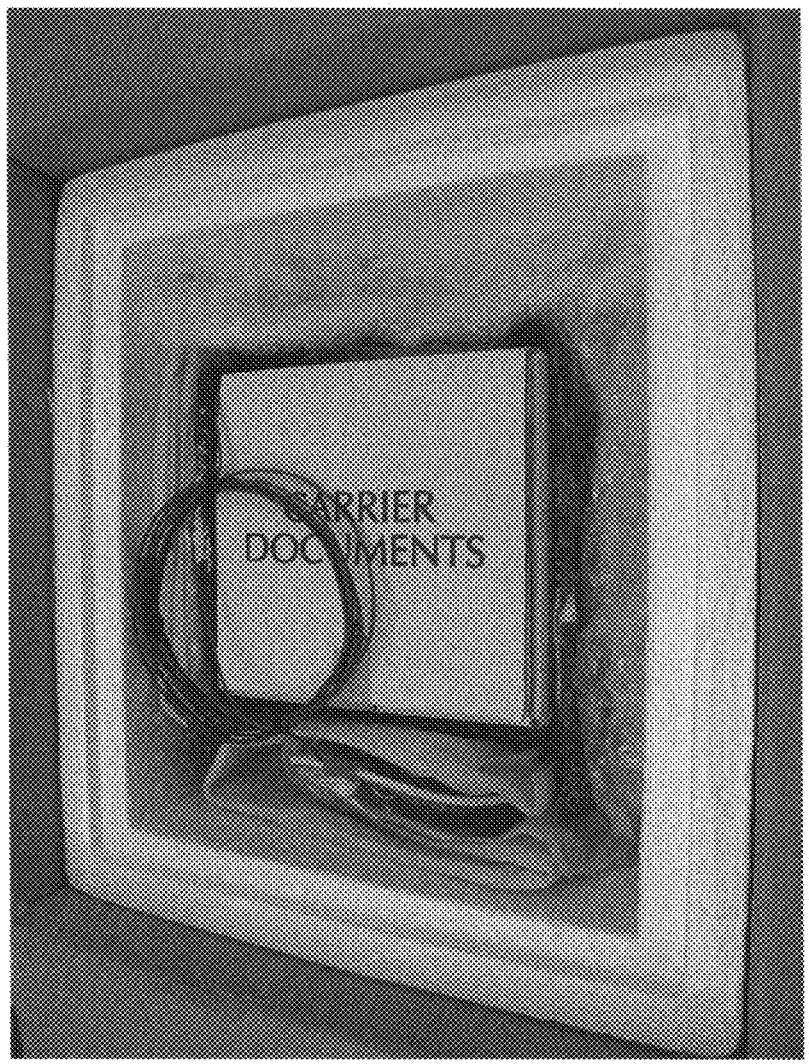

Once the neo-bladder has incubated in the bioreactor for 6 days, it is transported to the shipping container. In the studies described herein, the shipping container is a 1 liter NALGENE® polypropylene jar with a screw cap lid with a Teflon seal (FIG. 17). The NALGENE® jar contains an inner plastic basket which supports the neo-bladder during transport (FIG. 18). The neo-bladder can be secured to the inner support basket to prohibit movement during the shipping process (FIG. 19). The inner basket can also be removed at time of surgery. This enables the surgical team to remove the neo-bladder from the outside container, drain the medium, and then place the sterile neo-organ basket onto the surgical field. This shipping container is an original design and is manufactured by Tengion Inc. The NALGENE® shipping container was chosen for its size and volume requirements necessary for shipping. During shipping, the container is sealed and two layers of parafilm are wrapped around the edge of the lid to prohibit leakage. The shipping container is labeled and placed in a temperature controlled insulated box, sealed, and shipped (FIG. 20).

Example 5

Bladder Reconstruction

Following pretreatment with intramuscular injection of 0.1 mg of acepromazine for every kilogram of body weight, surgery is performed under inhalation anesthesia (flurothane) of about 25 to about 35 mg per kilogram of body weight with endotracheal aeration. About 500 mg of Cefazolin sodium is administered intravenously both preoperatively and intraoperatively. Additional treatment of subcutaneously Cefazolin sodium is administered for postoperative days at a dose of about 30 milligrams per kilogram body weight per day. Postoperative analgesic treatment is managed with subcutaneous injections of about 0.1 to about 0.6 milligrams of butorphanol per kilogram of body weight.

A midline laparotomy is performed, the bladder is exposed and both ureters are identified. The bladder wall is incised ventrally and both ureteric junctions are visualized and temporarily intubated with 4 F stents. A subtotal cystectomy is performed, sparing the trigone area bearing the urethra and ureteral junctions. The animals can receive either a bladder shaped polymer alone or a bladder shaped polymer coated with cells. A 10 F silicone catheter is inserted into the urethra from the trigone in a retrograde fashion. An 8 F suprapubic catheter is brought into the bladder lumen passing through a short submucosal tunnel in the trigonal region. The suprapubic catheter is secured to the bladder serosa with a pursestring suture of 40 chromic. The anastomosis between trigone and graft is marked at each quadrant with permanent polypropylene sutures for future graft site identification. To ensure adherence between the cell-seeded neo-bladder construct and the surrounding omentum tissue at the site of implantation and to ensure adherence within the omentum itself, fibrin glue is applied to the surrounding omentum. Alternatively, or in addition, the neo-bladder is covered with fibrin glue (Vitex Technologies Inc., New York, N.Y.). The omentum is wrapped and secured around the neo-reservoir. The abdomen is closed with three layers of 3-0 vicryl. After recovery from anesthesia, all animals wear restraint collars to avoid wound and catheter manipulation during the early postoperative period. The transurethral catheters are removed between postoperative days 4 and 7. Cystograms are performed about four weeks postoperatively, immediately prior to the suprapubic catheter removal. Cystograms and urodynamic studies are serially performed at about 1, about 2, about 3, about 4, about 6 and about 11 months after surgery.

Example 6

Analysis of Reconstructed Bladder

Urodynamic studies and radiographic cystograms are performed preoperatively and postoperatively at about 1, about 2, about 3, about 4, about 6, and about 11 months after surgery. Animals are sacrificed at about 1, about 2, about 3, about 4, about 6 and about 11 months after surgery. Bladders are retrieved for gross, histological and immunocytochemical analyses.

Urodynamic studies are performed using a 7 F double-lumen transurethral catheter. The bladders are emptied and intravesical pressures are recorded during instillation of pre-warmed saline solution at constant rates. Recordings are continued until leak point pressures (LPP) were reached. Bladder volume at capacity ($Vol_{max}$), LPP and bladder compliance ($Vol_{max}$/LPP) are documented. Bladder compliance, also called bladder elastance, denotes the quality of yielding to pressure or force without disruption. Bladder compliance is also an expression of the measure of the ability to yield to pressure or force without disruption, as an expression of the distensibility of the bladder. It is usually measured in units of volume change per unit of pressure change. Subsequently, radiographic cystograms are performed. The bladders are emptied and contrast medium is instilled intravesically under fluoroscopic control.

Example 7

Gross Findings

At the intended time points, the animals are euthanized by intravenous pentobarbital administration The internal organs and the urogenital tract are inspected for gross abnormalities. The bladder is retrieved and the marking sutures identifying the transition zone between native trigone and graft were exposed. Cross sections are taken from within the native trigone, the outlined transition zone and the proximally located neo-bladder.

Example 8

Histological and Immunocytochemical Findings

Specimens are fixed in 10% buffered formalin and processed. Tissue sections are cut at about 4 to about 6 microns for routine staining with Hematoxylin and Eosin (H&E) and Masson's trichrome. Immunocytochemical staining methods are employed with several specific primary antibodies in order to characterize urothelial and smooth muscle cell differentiation in the retrieved bladders. Anti-Desmin antibody (monoclonal NCL-DESDERII, clone DE-R-11, Novocastra®, Newcastle UK), which reacts with parts of the intermediate filament muscle cell protein desmin, and Anti-Alpha Smooth Muscle Actin antibody (monoclonal NCL-SMA, clone asm-1, Novocastra®, Newcastle UK), which labels ladder smooth muscle actin, are used as general markers for smooth muscle differentiation. Anti-Pancytokeratins AE1/AE3 antibody (monoclonal, Cat. No. 1124 161, Boehringer Mannheim®) and Anti-Cytokeratin 7 antibody (NCL-CK7, Clone LP5K, IgG2b, Novocastra®, New Castle, UK) which react against intermediate filaments that form part of the cytoskeletal complex in epithelial tissues, are used to identify urothelium. Anti-Asymmetric Unit Membrane (AUM) staining, using polyclonal antibodies, is used to investigate the presence of mammalian uroplakins, which form the apical plaques in mammalian urothelium and play an important functional role during advanced stages of urothelial differentiation. Anti S-100 antibody (Sigma®, St. Louis Mo., No. IMMH-9), reacting with the acidic calcium-binding protein S-100, mainly present in Schwann cells and glial elements in the nervous system, is used to identify neural tissues.

Specimens are fixed in Carnoy's solution or other acceptable fixative for immunohistochemical staining and routinely processed for immunostaining. High temperature antigen unmasking pretreatment with about 0.1% trypsin is performed using a commercially available kit according to the manufacturer's recommendations (Sigma®, St. Louis Mo., T-8 128). Antigen-specific primary antibodies are applied to the deparaffinized and hydrate tissue sections. Negative controls are treated with plain serum instead of the primary antibody. Positive controls consist of normal bladder tissue. After washing with phosphate buffered saline, the tissue sections are incubated with a biotinylated secondary antibody and washed again. A peroxidase reagent is added and upon substrate addition, the sites of antibody deposition are visualized by a brown precipitate. Counterstaining is performed with Gill's hematoxylin.

Example 9

Inserts for Vessel Attachments to Neo-Organ Scaffold

Flanged-Tube Inserts for Vessel Attachment to Neo-Organ. To facilitate attachment of a tubular vessel to a neo-organ scaffold or construct or the attachment of a neo-vessel scaffold or construct to a neo-organ scaffold or construct or to another tubular structure (e.g., blood vessel or another neo-vessel scaffold or construct), the scaffold material is formed in the shape of one or more flanged tubes. For example, in one embodiment of a neo-bladder construct, the urethra is fed through the interior of the tube, splatulated, and sutured to the leading surface of the flange. The insert is uncoated, partially coated, or coated, and may be reinforced with a woven mesh or suture, or other common reinforcing method. The insert is exemplified below using a neo-bladder scaffold design. However, it will be understood that the inserts described herein are useful in conjunction with a variety of neo-organ and neo-vessel scaffolds, including, for example, a neo-kidney scaffold, a neo-vessel scaffold and a neo-uterus scaffold.

Once the vessel, e.g., urethra, is attached to the insert, the flanged end is inserted into the interior of the organ or neo-organ construct, e.g., bladder or neo-bladder, through a hole, receptacle, or port, adapted to receive a tubular vessel or insert, (e.g., a neo-bladder construct of the type illustrated in FIGS. 21, 26 and 27) or at the distal ends of the elliptical, longitudinal opening, (e.g., a neo-bladder construct on the type illustrated in FIGS. 8-10), while the tubular portion of the insert remains outside the organ or neo-organ construct. The edges of the hole, receptacle, or port in the neo-bladder construct surface (e.g., a neo-bladder construct of the type illustrated in FIG. 21) are notched to form flaps, allowing the larger flange portion to enter, and then close the hole around the insert. In one embodiment, the hole, receptacle, or port is exactly the outer diameter of the tubular section of the insert, so after the insert is in place, the closed flaps lay flat on the side of the flange. FIGS. 21A-21D depict an assembled two-part neo-bladder construct with ports adapted to receive tubular inserts and the flanged inserts located therein.

In another embodiment, the flaps are lifted and pulled out from the neo-bladder construct, the insert is placed, and the flaps allowed to rest against the side tube section of the insert. The flaps are then sutured closed. The neo-bladder construct is shipped with the flaps loosely sutured, so that the surgeon only needs to pull the sutures tight to close and tighten the flaps. In addition, the flaps could be sutured to the tube section of the insert in order to increase stability of the insert-urethra element.

The inserts described herein have several advantages over current methods for attaching vessels to tissue-engineered cell matrix constructs. For example, in the case of the bladder, when inserts are used, the surgeon only needs to suture (or otherwise attach) the urethra or ureters to the insert, not to the neo-bladder construct directly. The inserts are much smaller and easier to work with than the neo-bladder construct, thus decreasing the length of surgery time. Also, if the insert is not seeded with cells, it can be handled extensively without fear of damaging cells.

In addition, the use of inserts allows the cells on the neo-bladder construct to remain in the medium and be exposed for a much shorter time. Without inserts, the neo-bladder construct is typically removed from the medium and remains exposed to the atmosphere while all of the vessels are sutured onto it. With this system, the neo-bladder construct will stay in the liquid medium until all of the suturing of the vessels to the inserts is completed.

Furthermore, the use of inserts allows the neo-bladder construct to be shipped to the surgeon as an intact sphere, quasi-sphere, hemisphere, or quasi-hemisphere, with holes, receptacles, or ports adapted to receive the tubular vessel or insert, and flaps for the vessels or inserts. In this case, the surgeon would not need to join the two halves of the neo-bladder construct together in the operating suite. In addition, since the flanged tubes are not attached to the neo-bladder construct prior to the time of implantation, they will produce no torque or strain on the construct during culture and shipping. Moreover, several inserts in a range of sizes could be supplied to the surgeon to account for inter-patient variation.

Flanged Tube Inserts with Washers.

Figure 22:
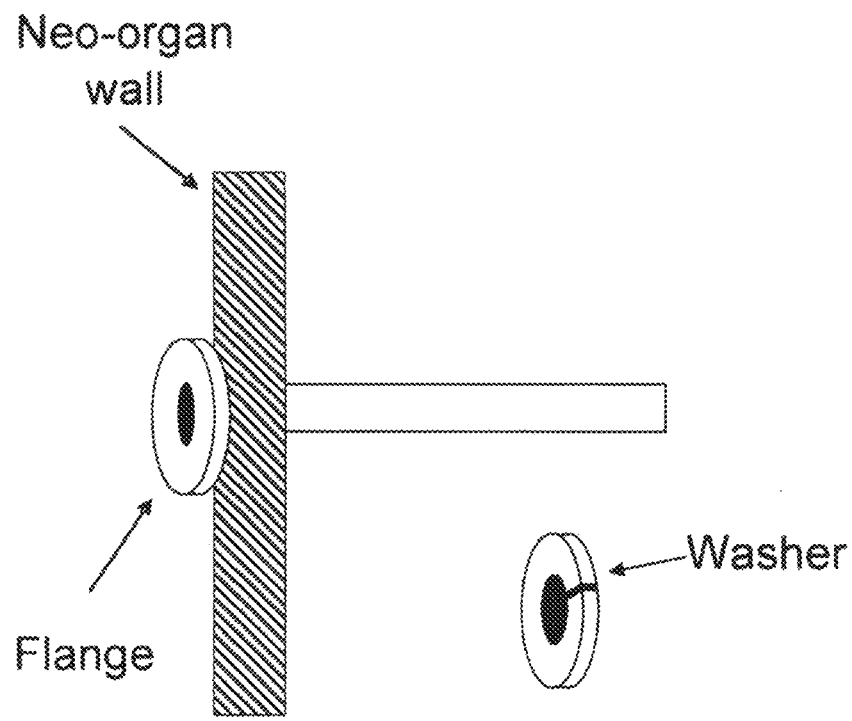
FIG. 22 depicts a tubular vessel with a flange at the end after being inserted through a receptacle or port of a neo-organ matrix or scaffold wall (shown in cross section) and a washer.

The neo-organ scaffolds and constructs described in this embodiment use preformed insets, holes, receptacles, or ports, adapted to receive a tubular vessel or insert, to which the tubular vessels or inserts are attached prior to implantation of the neo-organ scaffold or construct, which will take place after the neo-bladder construct is set into place. This insert has a flange at the end closest to the neo-bladder scaffold or construct and a washer (FIG. 22). The washer can be any shape or size that is suitable for the site of implantation. The washer can be made from any material suitable for use at the site of implantation. The vessel is run through the insert, which has a washer positioned on the insert tube proximal to the flange. The forward end of the vessel is splayed, and sutured or glued onto the leading face of the flange. The flanged, tubular vessel construct will be inserted into the neo-bladder scaffold or construct, through a hole, receptacle, or port adapted to receive the inert, so that the neo-bladder scaffold or construct is between the flange and the washer. The flange is then brought into contact with the interior surface of the scaffold or construct wall and the washer is brought into contact with the external surface of the scaffold or construct wall, the flange and washer thus "sandwiching" the scaffold or construct wall. This sandwiched area may then be sutured to the washer, giving added strength to this joint.

Self Stabilizing Inserts for Attachment of Vessels to a Neo Organ Construct.

Figure 23:
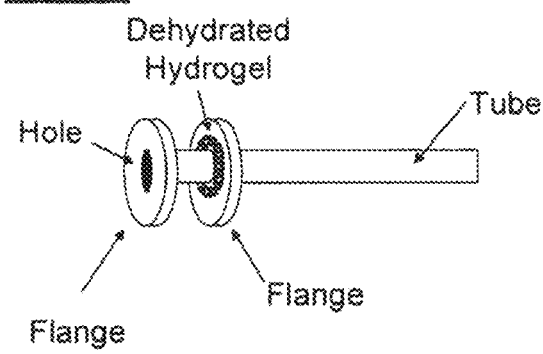
FIG. 23 depicts a flanged tubular vessel or insert for the attachment of tubular vessels to a neo-organ matrix or scaffold prior to insertion into the scaffold wall, shown with washer near the flanged end with a dehydrated hydrogel located on the side of the washer proximal to the flange.
Figure 24:
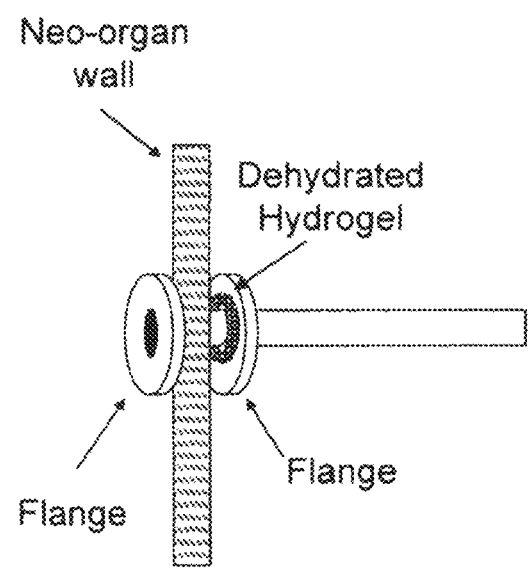
FIG. 24 depicts the insert shown in FIG. 23 after the flanged end has been inserted through the wall of a neo-organ matrix or scaffold. The remainder of the insert stays on the other side of the scaffold wall.
Figure 25:
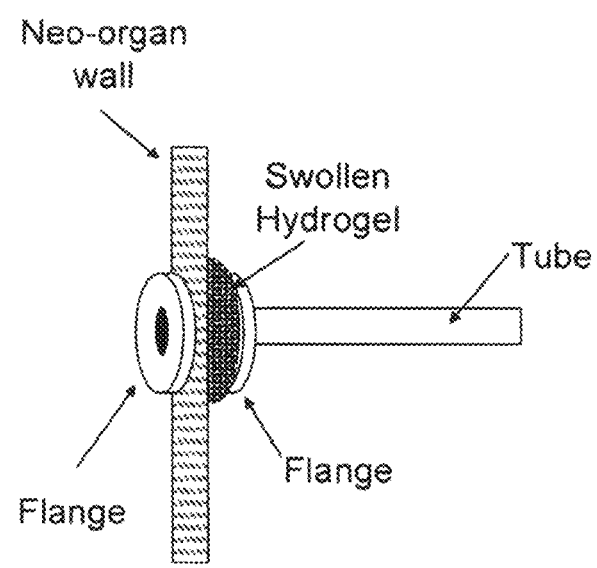
FIG. 25 depicts the insert of FIG. 24 after the hydrogel has been swollen, thereby filling the space between the outer flange and the neo-organ scaffold wall.

The inserts described herein use "gaskets" of a swellable, biodegradable material (hydrogel) to firmly attach inserts into a hollow neo-organ scaffold or construct. This insert has two flanges instead of one at the end closest to the neo-organ. The dehydrated hydrogel is located between the flanges. The flanged, tubular insert construct is inserted into the neo-organ scaffold or construct, so that the scaffold or construct wall is between the two flanges. The hydrogel then swells, forming a tight seal, thereby attaching the insert to the neo-organ scaffold or construct and preventing leakage around the insert, which, in turn, eliminates the need for suturing and shortens operating time. As depicted in FIGS. 23-25, the insert would have two flanges at one end, with the dehydrated hydrogel in between. The hydrogel could be in the form of a washer, two or more washers, a coating on one flange, or coating on both flanges. After the vessel is attached to the insert as described above, the first flange is inserted through the wall of the neo-organ scaffold or construct. With the wall between the two flanges, the hydrogel is swollen, filling the gap between the flanges and pulling them tight against the neo-organ scaffold or construct wall. This will prevent movement of the interior flange with respect to the wall, allowing for cell migration between them and tissue regeneration across the boundary. In addition, the swollen hydrogel prevents leakage through the hole in the wall around the outside of the tube. Thus, the swollen hydrogel eliminates the need for suturing the wall closed and for suturing or otherwise fixing the insert in place. Over time, as the tissue regenerates and the vessel attaches to the neo-organ construct, the hydrogel will degrade in a manner similar to the other scaffold material.

The swellable, biodegradable hydrogel could consist of a variety of materials, including, but not limited to: cellulosics, starches, gelatins, collagen, chitosan, crosslinked proteins, poly(ethylene oxide) (PEO), copolymers of PEO with other biodegradable polymers, such as polyglycolic acid, polylactic acid, polylactic-co-glycolic acid, acrylates, polyesters, etc., acrylates modified to be biodegradable, interpenetrating networks and semi-interpenetrating networks. In some embodiments, the hydrogel swells simply by exposure to water of body fluid. Alternatively, or in addition, the hydrogel could swell in response to a stimulus, such as a particular ionic concentration, pH, osmololality, or temperature change. The rate at which the hydrogel swells can be controlled by means of chemical composition, current hydration state, ion concentration, and other means. The hydrogel could be contained in a non-hydrogel membrane which possesses appropriate material properties, such as strength, toughness and pliability.

Assembled Two-Part Neo-Bladder Replacement Implant with Inserts.

Figure 26:
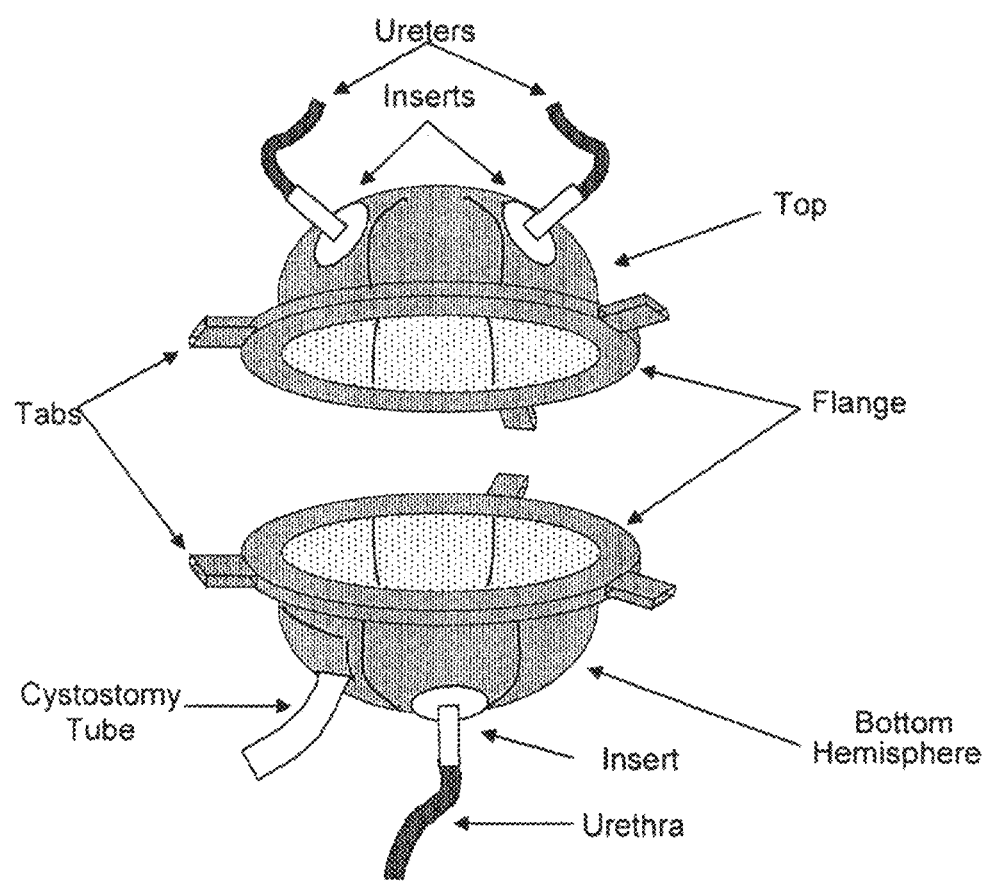
FIG. 26 is an illustration depicting a two-part neo-organ matrix or scaffold for bladder replacement. Each scaffold portion includes one or more unseeded tabs, a flange, and at least one receptacle or port to accept a flanged insert for attachment of a tubular vessel.
Figure 27:
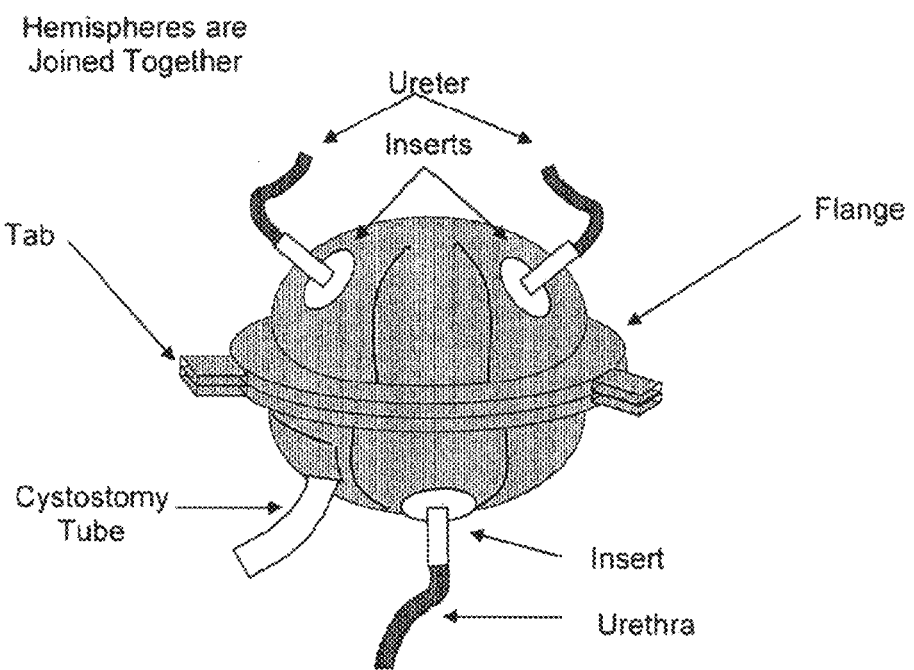
FIG. 27 is an illustration depicting the scaffold of FIG. 26 after the two hemispherical neo-organ matrix or scaffolds have been joined.
Figure 28:
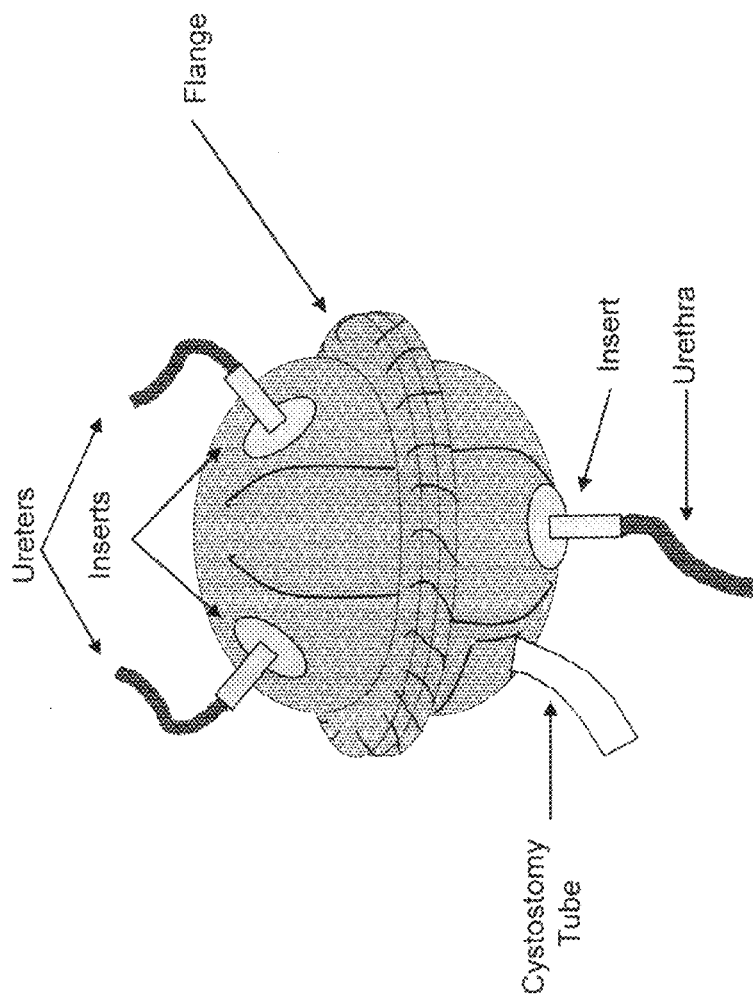
FIG. 28 is an illustration depicting the scaffold of FIG. 27 after the two joined hemispherical scaffold portions have been sutured together and the tabs have been removed. The joined flange surfaces may be trimmed at this stage.

The two part hollow neo-bladder replacement scaffold or construct shown in FIGS. 26-28 incorporates the flanged inserts, unseeded tabs and flanged rims described above, and additionally, each half is comprised of a single-piece each. The separate pieces or hemispheres may be sutured together to form a single spherical neo-organ scaffold prior to or after coating and cell seeding. The unseeded tabs are used for maneuvering the construct parts during implantation, and the unseeded flanges are used to increase the ease of securing the two halves together. Vessels are attached to the inserts prior to implantation of the scaffold or construct. Once the neo-organ scaffold or construct is secured, the vessels are 'plugged' into place, thus completing the neo-bladder construct in vivo.

Example 10

Use of the Two-Part Neo-Bladder Construct in Trigone-Sparing Augmentation

Figure 29A:
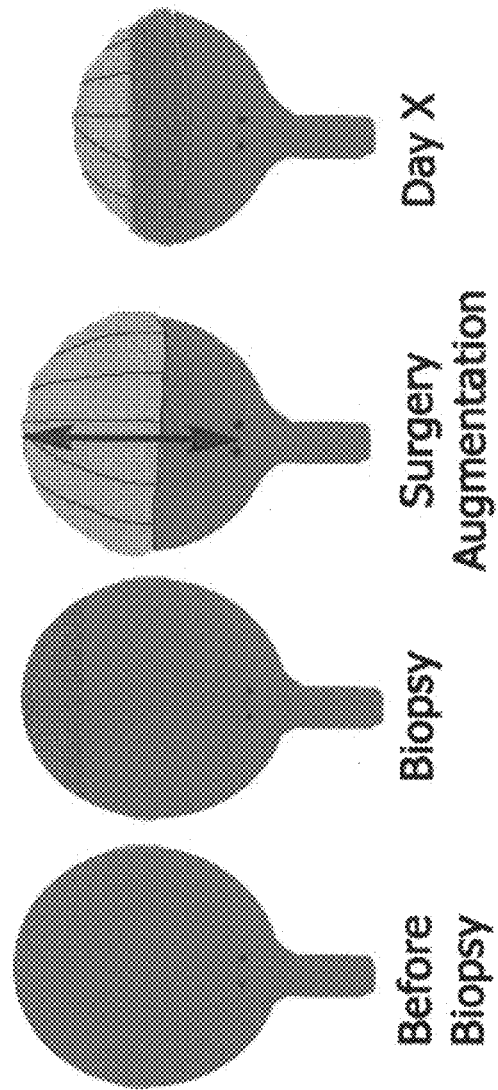
FIGS. 29A-29B are a series of illustrations depicting trigone-sparing bladder augmentation surgery.
Figure 29B:
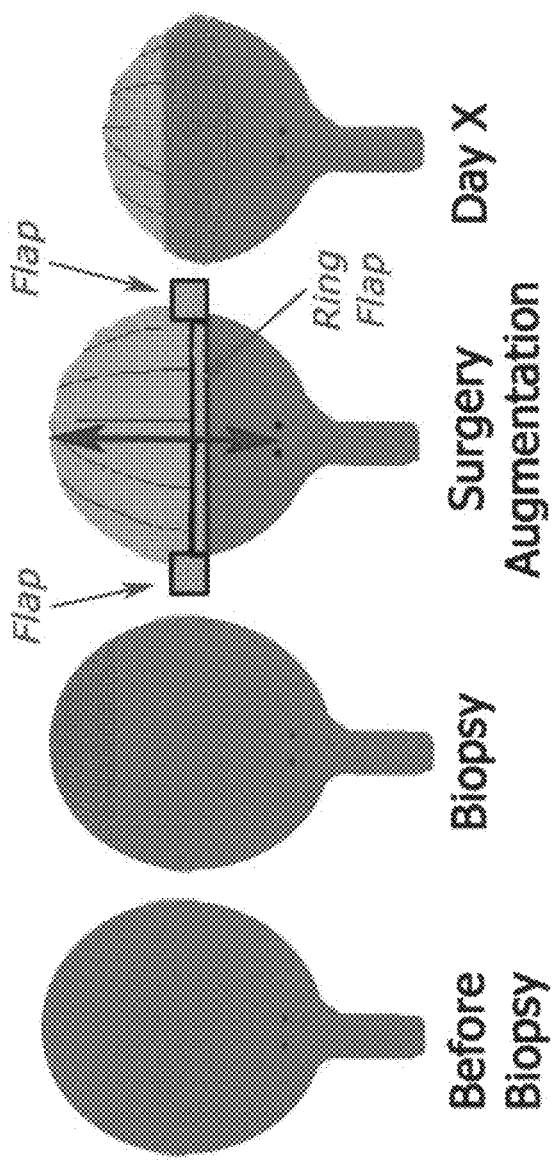

The illustration shown in FIG. 29A depicts the use of an initial augmentation construct design consisting of a one-piece, non-flanged construct design during experimental surgical manipulations at the time of trigone-sparing surgical augmentation. FIG. 29B, in contrast, depicts the use of a two-part construct comprising a cell seeded dome shaped, flanged construct and a separate flanged collar, as described above in Example 1 and depicted in FIG. 2.

Surgical protocol for the implantation of a neo-bladder construct requires the use of the patient's omental tissue. The omental tissue mass and volume reflects individual variability and is affected by disease processes. Therefore, an early, but critical, surgical manipulation in the implantation of a neo-bladder construct is the extraction of the abdominal mesenteric omentum. Once the neo-bladder construct is taken out of the transport media, to protect the cells, it is critical for the surgeon not to touch the surfaces of the neo-bladder to be implanted. Therefore, the original neo-bladder design shown in FIG. 29A caused problems for the surgeon; requiring additional surgical tools and surgical time (see FIG. 29C). The two-part neo-bladder augmentation construct shown in FIG. 29B alleviates these problems. As described above, the two-part augmentation design includes unseeded flaps or tabs and an outer ring or brim for ease of manipulation. The two part neo-bladder augmentation construct shown in FIGS. 7-10 was designed to further alleviate these problems.

Example 11

Use of the Two-Part Neo-Bladder Construct in Non-Trigone-Sparing Augmentation (Full Bladder Replacement)

Full Bladder Replacement Pilot Test Results.

Figure 30:
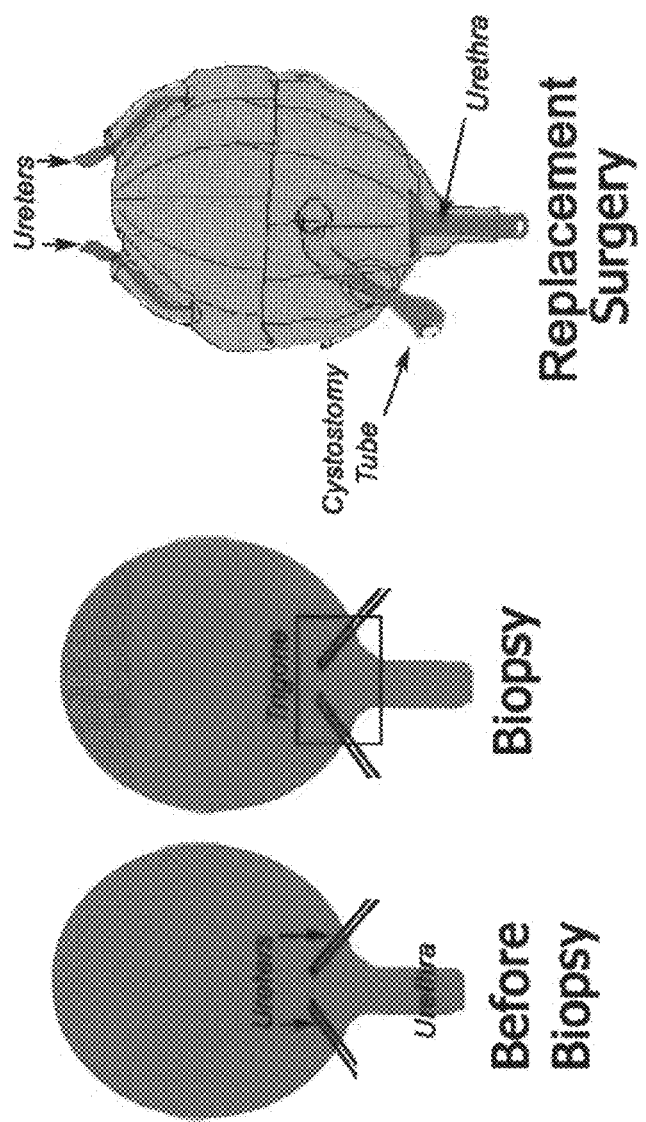
FIG. 30 is an illustration depicting non-trigone sparing bladder replacement surgery using a previous neo-organ replacement construct design.

The illustration presented in FIG. 30 depicts the experimental surgical manipulation at the time of the non-Trigone-sparing surgical replacement with an initial neo-bladder construct design, using tunnels to guide ureters and urethra into place, for spatulation.

Figure 31:
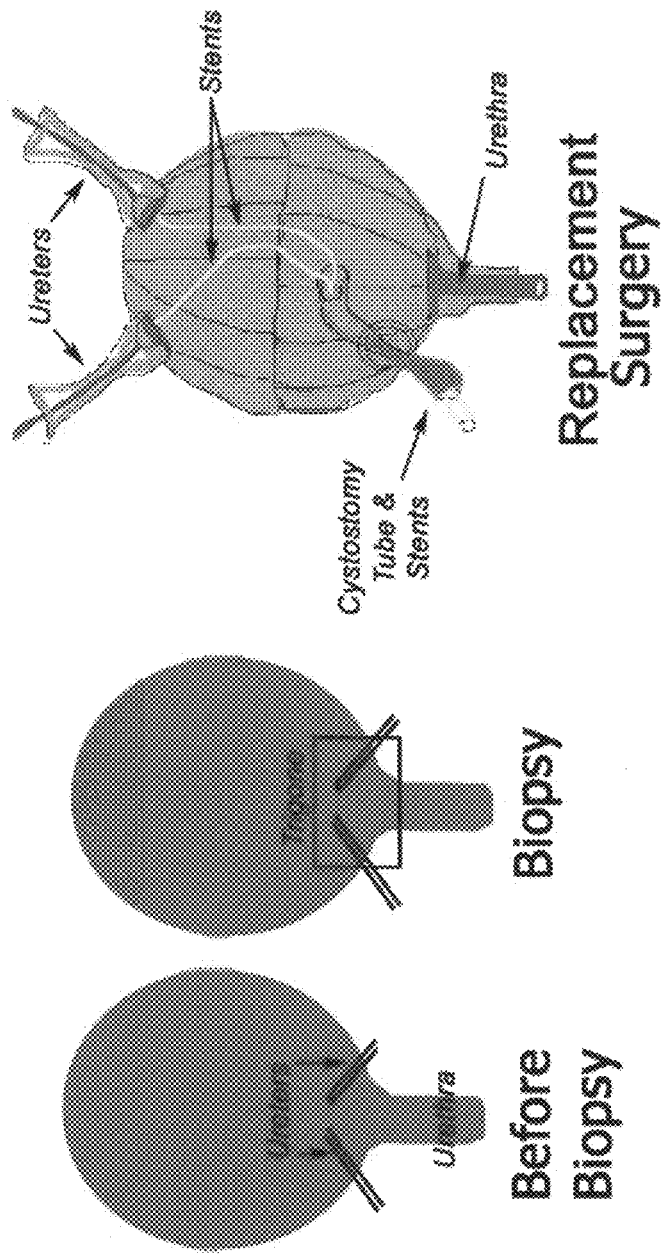
FIG. 31 is an illustration depicting non-trigone sparing bladder replacement surgery using a modified neo-organ replacement construct design that includes receptacles or ports adapted to receive a tubular vessel or insert, for the attachment of the ureters and the urethra.

Previous studies involving bladder replacement surgery using the initial two-piece construct design shown in FIG. 30 were unsuccessful. Accordingly, the neo-bladder replacement implant design was modified to include tubes instead of tunnels for ureter attachment, as illustrated in FIGS. 21, 26 and 27. FIG. 31 depicts the modified neo-bladder replacement implant design and the inclusion of stents used in the non-Trigone-sparing surgical replacement.

Additional bladder replacement studies were also unsuccessful. However, it was determined that the modified ureteral attachments to the neo-bladder, plus the use of the stents, prevented any block of the renal outflow into the neo-bladder. The replacement construct was then redesigned to produce a scaffold such as the assembled construct shown in FIGS. 8-10.

It is understood that the disclosed methods are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed invention belongs.

Those skilled in the art will recognize, or be able to ascertain using no more than routine experimentation, many equivalents to the specific embodiments of the invention described herein. Such equivalents are intended to be encompassed by the following claims.

We claim:

1. An implantable construct comprising:
   (a) a first hemispherical matrix and a second hemispherical matrix each having a first surface, a closed end, and an open equatorial border comprising a flanged region, wherein the first matrix and the second matrix are adapted to mate and are shaped to conform to at least a part of a luminal organ when mated, wherein the first matrix, the second matrix, or both, are each adapted to receive a native vessel, and wherein the flanged region of the first matrix is adapted to mate with the flanged region of the second matrix; and
   (b) a first cell population deposited on or in said first surface of the first matrix and on or in said first surface of the second matrix to form an implantable construct, wherein said first cell population comprises a muscle cell population, said matrices and said cell population forming an implantable construct.

2. The construct of claim 1, wherein the first matrix, the second matrix, or both, further comprise at least one receptacle.

3. The construct of claim 2, wherein the at least one receptacle is adapted to receive a tubular insert.

4. The construct of claim 3, further comprising a tubular insert which is disposed within said at least one receptacle, wherein the tubular insert has an end.

5. The construct of claim 4, the tubular insert having at least one flange located at said end.

6. The construct of claim 4, wherein the tubular insert is adapted to connect to a native vessel.

7. The construct of claim 5, further comprising a surface and a washer disposed around the tubular insert.

8. The construct of claim 7, wherein the washer is adapted to form a watertight seal between the flange and the surface of the construct.

9. The construct of claim 7 or 8, wherein said washer comprises a hydrogel.

10. The construct of claim 1, wherein the first matrix, second matrix, or both, comprise a biocompatible material.

11. The construct of claim 10, wherein the biocompatible material comprises a biodegradable material.

12. The construct of claim 1, wherein the first matrix, second matrix, or both, comprise material selected from the group consisting of polyglycolic acid, polylactic acid and a copolymer of glycolic acid and lactic acid.

13. The construct of claim 1, wherein the first matrix, second matrix, or both, comprise polyglycolic acid and a copolymer of glycolic acid and lactic acid.

14. The construct of claim 1, wherein the at least one cell population is a smooth muscle cell population.

15. The construct of claim 1, said matrices each having a second surface, the construct further comprising a second population of cells deposited on or in said second surface of the first matrix, said second surface of the second matrix, or both.

16. The construct of claim 15, wherein the second population of cells comprises urothelial cells.

17. The construct of claim 1, wherein the luminal organ is a genitourinary organ.

18. The construct of claim 17, wherein the genitourinary organ is selected from the group consisting of bladder, ureters and urethra.

19. The construct of claim 17, wherein the genitourinary organ is a bladder or a bladder segment.

20. The construct of claim 19, wherein the implantable construct is adapted to form regenerated bladder tissue in vivo that exhibits the compliance of natural bladder tissue.

21. The construct of claim 1, wherein the first matrix has a hemispherical shape having a closed end and an open, equatorial border, and wherein the second matrix comprises a collar adapted to mate with the equatorial border of the first matrix.

22. The construct of claim 21, said matrices comprising second surfaces, the construct further comprising a second population of cells deposited on or in a second surface of the first matrix, a second surface of the second matrix, or both.

23. The construct of claim 22, wherein the second population of cells comprises urothelial cells.

24. The construct of claim 23, wherein one of the first or second population of cells are not deposited on or in the first or second surface of the collar-shaped second matrix.

25. The construct of claim 1, further comprising a second population of cells deposited on or in a second surface of the first matrix, a second surface of the second matrix, or both.

26. The construct of claim 25, wherein the second population of cells comprises urothelial cells.

27. The construct of claim 1, wherein the open equatorial border of the first matrix is adapted to mate with the open equatorial border of the second matrix.

28. The construct of claim 27, wherein each open equatorial border is a flanged equatorial border.

29. A method for the reconstruction, augmentation or replacement of laminarly organized luminal organs or tissue structures in a patient in need of such treatment comprising implanting the construct of claim 1 into said patient at the site of said treatment for the regeneration of a luminal organ or tissue structure.

30. The method of claim 29, wherein the first matrix, second matrix, or both, is adapted to receive a native vessel.

31. The method of claim 30, wherein the first matrix, second matrix, or both, further comprise at least one receptacle.

32. The method of claim 31, wherein the at least one receptacle is adapted to receive a tubular insert.

33. The method of claim 32, wherein the first matrix, second matrix, or both, further comprise a tubular insert which is disposed within the at least one receptacle, wherein the tubular insert has an end.

34. The method of claim 33, the tubular insert having at least one flange located at said end.

35. The method of claim 34, wherein the tubular insert is adapted to connect to a native vessel.

36. The method of claim 35, wherein the first matrix, second matrix, or both, further comprise a surface and a washer disposed around the tubular insert.

37. The method of claim 36, wherein the washer is adapted to form a watertight seal between the flange and the surface of the construct.

38. The method of claim 35 or 36, wherein said washer comprises a hydrogel.

* * * * *